United States Patent
Lee et al.

(10) Patent No.: US 7,947,051 B2
(45) Date of Patent: *May 24, 2011

(54) SURGICAL INSTRUMENT COUPLING MECHANISM

(75) Inventors: Woojin Lee, Hopkinton, MA (US);
Michael J. Mazzuca, North Easton, MA (US); Michael C. Gorhan, Mansfield, MA (US)

(73) Assignee: Hansen Medical, Inc., Mountain View, CA (US)

( * ) Notice: Subject to any disclaimer, the term of this patent is extended or adjusted under 35 U.S.C. 154(b) by 1009 days.

This patent is subject to a terminal disclaimer.

(21) Appl. No.: 11/762,745

(22) Filed: Jun. 13, 2007

(65) Prior Publication Data

US 2007/0238925 A1     Oct. 11, 2007

Related U.S. Application Data

(63) Continuation of application No. 10/302,804, filed on Nov. 21, 2002, now Pat. No. 7,331,967.

(60) Provisional application No. 60/409,530, filed on Sep. 9, 2002.

(51) Int. Cl.
*A61B 19/00* (2006.01)

(52) U.S. Cl. ........................... 606/130; 600/407

(58) Field of Classification Search .................. 606/130; 600/101, 102, 109, 114, 229, 234, 235, 407, 600/429; 700/85, 245, 247
See application file for complete search history.

(56) References Cited

U.S. PATENT DOCUMENTS

| | | |
|---|---|---|
| 3,270,572 A | 9/1966 | Zimmerle et al. |
| 3,347,111 A | 10/1967 | Rouillard et al. |
| 4,234,210 A | 11/1980 | McNally et al. |
| 4,283,165 A | 8/1981 | Vertut |
| 4,507,044 A | 3/1985 | Hutchins et al. |
| 4,604,016 A | 8/1986 | Joyce |
| 4,941,454 A | 7/1990 | Wood et al. |
| 4,979,949 A | 12/1990 | Matsen, III et al. |
| 5,048,529 A | 9/1991 | Blumenthal |
| 5,063,334 A | 11/1991 | Tanita et al. |
| 5,078,140 A | 1/1992 | Kwoh |
| 5,086,401 A | 2/1992 | Glassman et al. |
| 5,154,717 A | 10/1992 | Matsen, III et al. |
| 5,184,601 A | 2/1993 | Putman |
| 5,207,114 A | 5/1993 | Salisbury, Jr. et al. |

(Continued)

FOREIGN PATENT DOCUMENTS

JP          05118212          11/1994

(Continued)

*Primary Examiner* — Kevin T Truong
(74) *Attorney, Agent, or Firm* — Vista IP Law Group LLP

(57) ABSTRACT

A medical system and surgical instrument adapter are provided. The medical system comprises a surgical instrument carrying a distal tool configured for performing a medical procedure on a patient, an adapter having a clam-shell configuration configured for removably receiving a proximal end of the surgical instrument, and a drive unit configured for being coupled to the adapter to control the movement of the surgical instrument within at least one degree-of-freedom. The surgical instrument adapter may comprise a base portion configured for receiving a proximal end of the surgical instrument, and a clam-shell that pivots relative to the base portion between a first position that encloses the proximal end of the surgical instrument within the base portion and a second position that allows the proximal end of the surgical instrument to be removed from the base portion.

22 Claims, 16 Drawing Sheets

U.S. PATENT DOCUMENTS

| | | | |
|---|---|---|---|
| 5,217,003 A | 6/1993 | Wilk | |
| 5,236,432 A | 8/1993 | Matsen, III et al. | |
| 5,299,288 A | 3/1994 | Glassman et al. | |
| 5,324,163 A | 6/1994 | Costa | |
| 5,339,799 A | 8/1994 | Kami et al. | |
| 5,372,147 A | 12/1994 | Lathrop, Jr. et al. | |
| 5,382,885 A | 1/1995 | Salcudean et al. | |
| 5,397,323 A | 3/1995 | Taylor et al. | |
| 5,402,801 A | 4/1995 | Taylor | |
| 5,410,638 A | 4/1995 | Colgate et al. | |
| 5,417,210 A | 5/1995 | Funda et al. | |
| 5,515,478 A | 5/1996 | Wang | |
| 5,524,180 A | 6/1996 | Wang et al. | |
| 5,528,948 A | 6/1996 | De Gelis | |
| 5,540,649 A | 7/1996 | Bonnell et al. | |
| 5,553,198 A | 9/1996 | Wang et al. | |
| 5,572,999 A | 11/1996 | Funda et al. | |
| 5,611,248 A | 3/1997 | Peltier | |
| 5,624,398 A | 4/1997 | Smith et al. | |
| 5,631,973 A | 5/1997 | Green | |
| 5,640,883 A | 6/1997 | Takizawa | |
| 5,649,956 A | 7/1997 | Jensen et al. | |
| 5,657,429 A | 8/1997 | Wang et al. | |
| 5,722,909 A | 3/1998 | Thomey | |
| 5,754,741 A | 5/1998 | Wang et al. | |
| 5,762,458 A | 6/1998 | Wang et al. | |
| 5,784,542 A | 7/1998 | Ohm et al. | |
| 5,792,135 A | 8/1998 | Madhani et al. | |
| 5,800,333 A | 9/1998 | Liprie | |
| 5,800,423 A | 9/1998 | Jensen | |
| 5,807,377 A | 9/1998 | Madhani et al. | |
| 5,808,665 A | 9/1998 | Green | |
| 5,810,880 A | 9/1998 | Jensen et al. | |
| 5,815,640 A | 9/1998 | Wang et al. | |
| 5,816,770 A | 10/1998 | Itagaki | |
| 5,821,920 A | 10/1998 | Rosenberg et al. | |
| 5,825,982 A | 10/1998 | Wright et al. | |
| 5,828,197 A | 10/1998 | Martin et al. | |
| 5,833,656 A | 11/1998 | Smith et al. | |
| 5,855,553 A | 1/1999 | Tajima et al. | |
| 5,855,583 A | 1/1999 | Wang et al. | |
| 5,876,325 A | 3/1999 | Mizuno et al. | |
| 5,878,193 A | 3/1999 | Wang et al. | |
| 5,907,664 A | 5/1999 | Wang et al. | |
| 5,954,692 A | 9/1999 | Smith et al. | |
| 5,971,976 A | 10/1999 | Wang et al. | |
| 5,976,122 A | 11/1999 | Madhani et al. | |
| 6,001,108 A | 12/1999 | Wang et al. | |
| 6,007,550 A | 12/1999 | Wang et al. | |
| 6,036,636 A | 3/2000 | Motoki et al. | |
| 6,046,563 A | 4/2000 | Moreyra | |
| 6,063,095 A | 5/2000 | Wang et al. | |
| 6,070,480 A | 6/2000 | Kerschner | |
| 6,080,181 A | 6/2000 | Jensen et al. | |
| 6,096,004 A | 8/2000 | Meglan et al. | |
| 6,102,850 A | 8/2000 | Wang et al. | |
| 6,120,433 A | 9/2000 | Mizuno et al. | |
| 6,132,441 A | 10/2000 | Grace | |
| 6,197,017 B1 | 3/2001 | Brock et al. | |
| 6,206,903 B1 | 3/2001 | Ramans | |
| 6,223,100 B1 | 4/2001 | Green | |
| 6,231,565 B1 | 5/2001 | Tovey et al. | |
| 6,233,504 B1 | 5/2001 | Das et al. | |
| 6,246,200 B1 | 6/2001 | Blumenkranz et al. | |
| 6,264,419 B1 | 7/2001 | Schinzel | |
| 6,285,902 B1 * | 9/2001 | Kienzle et al. | 600/427 |
| 6,290,675 B1 | 9/2001 | Vujanic et al. | |
| 6,309,397 B1 | 10/2001 | Julian et al. | |
| 6,312,435 B1 | 11/2001 | Wallace et al. | |
| 6,325,808 B1 | 12/2001 | Bernard et al. | |
| 6,331,181 B1 | 12/2001 | Tierney et al. | |
| 6,346,072 B1 | 2/2002 | Cooper | |
| 6,364,888 B1 | 4/2002 | Niemeyer et al. | |
| 6,371,907 B1 | 4/2002 | Hasegawa et al. | |
| 6,375,471 B1 | 4/2002 | Wendlandt et al. | |
| 6,377,011 B1 | 4/2002 | Ben-Ur | |
| 6,385,509 B2 | 5/2002 | Das et al. | |
| 6,394,998 B1 | 5/2002 | Wallace et al. | |
| 6,398,726 B1 | 6/2002 | Ramans et al. | |
| 6,432,112 B2 | 8/2002 | Brock et al. | |
| 6,436,107 B1 | 8/2002 | Wang et al. | |
| 6,441,577 B2 | 8/2002 | Blumenkranz et al. | |
| 6,451,027 B1 | 9/2002 | Cooper et al. | |
| 6,459,926 B1 | 10/2002 | Nowlin et al. | |
| 6,463,361 B1 | 10/2002 | Wang et al. | |
| 6,468,265 B1 | 10/2002 | Evans et al. | |
| 6,490,490 B1 | 12/2002 | Uchikubo et al. | |
| 6,491,691 B1 | 12/2002 | Morley et al. | |
| 6,491,701 B2 | 12/2002 | Tierney et al. | |
| 6,493,608 B1 | 12/2002 | Niemeyer et al. | |
| 6,496,099 B2 | 12/2002 | Wang et al. | |
| 6,517,565 B1 | 2/2003 | Whitman et al. | |
| 6,522,906 B1 | 2/2003 | Salisbury, Jr. et al. | |
| 6,554,844 B2 | 4/2003 | Lee et al. | |
| 6,565,554 B1 | 5/2003 | Niemeyer | |
| 6,587,750 B2 | 7/2003 | Gerbi et al. | |
| 6,594,552 B1 | 7/2003 | Nowlin et al. | |
| 6,620,173 B2 | 9/2003 | Gerbi et al. | |
| 6,645,196 B1 | 11/2003 | Nixon et al. | |
| 6,676,684 B1 | 1/2004 | Morley et al. | |
| 6,685,698 B2 | 2/2004 | Morley et al. | |
| 6,692,485 B1 | 2/2004 | Brock et al. | |
| 6,697,664 B2 * | 2/2004 | Kienzle, III et al. | 600/427 |
| 6,699,235 B2 | 3/2004 | Wallace et al. | |
| 6,720,988 B1 | 4/2004 | Gere et al. | |
| 6,726,675 B1 | 4/2004 | Beyar | |
| 6,726,699 B1 | 4/2004 | Wright et al. | |
| 6,728,599 B2 | 4/2004 | Wang et al. | |
| 6,770,081 B1 | 8/2004 | Cooper et al. | |
| 6,783,524 B2 | 8/2004 | Anderson et al. | |
| 6,788,018 B1 | 9/2004 | Blumenkranz | |
| 6,793,653 B2 | 9/2004 | Sanchez et al. | |
| 6,799,065 B1 | 9/2004 | Niemeyer | |
| 6,817,972 B2 | 11/2004 | Snow | |
| 6,817,974 B2 | 11/2004 | Cooper et al. | |
| 6,837,883 B2 | 1/2005 | Moll et al. | |
| 6,840,938 B1 | 1/2005 | Morley et al. | |
| 6,852,107 B2 | 2/2005 | Wang et al. | |
| 6,860,877 B1 | 3/2005 | Sanchez et al. | |
| 6,911,916 B1 | 6/2005 | Wang et al. | |
| 6,936,001 B1 | 8/2005 | Snow | |
| 6,951,535 B2 | 10/2005 | Ghodoussi et al. | |
| 6,994,708 B2 | 2/2006 | Manzo | |
| 7,025,064 B2 | 4/2006 | Wang et al. | |

FOREIGN PATENT DOCUMENTS

| | | |
|---|---|---|
| JP | 09063668 | 9/1998 |
| WO | WO 98/25666 | 6/1998 |
| WO | WO 00/60521 | 10/2000 |
| WO | WO 00/67640 | 11/2000 |
| WO | WO 02/74178 | 2/2002 |

* cited by examiner

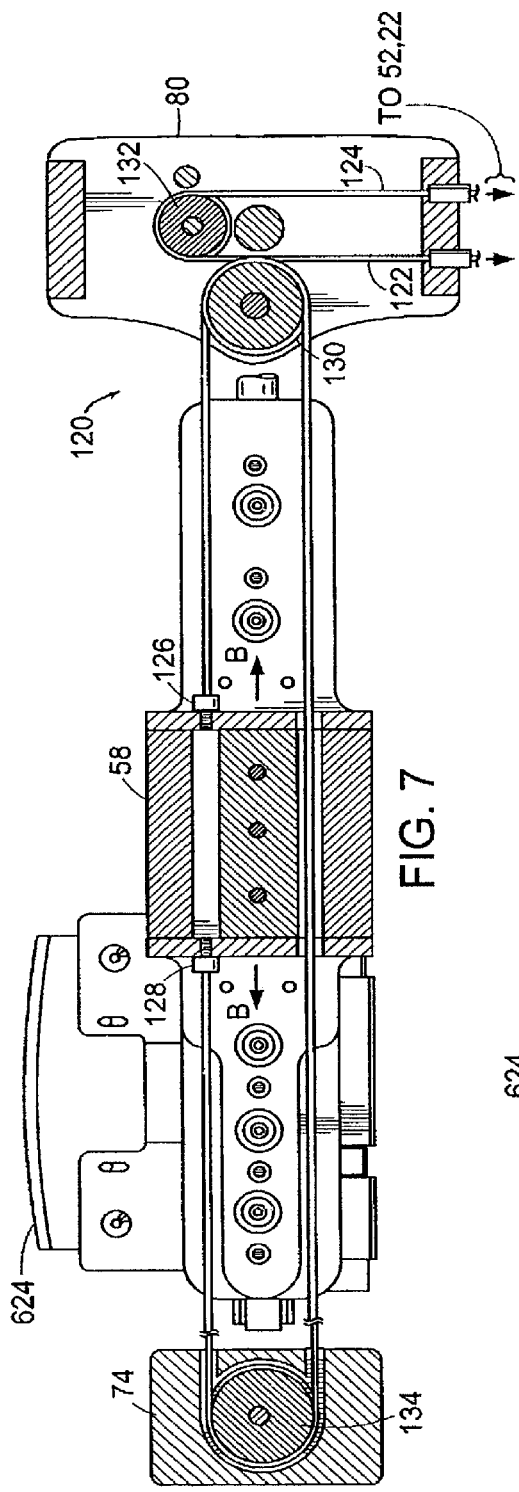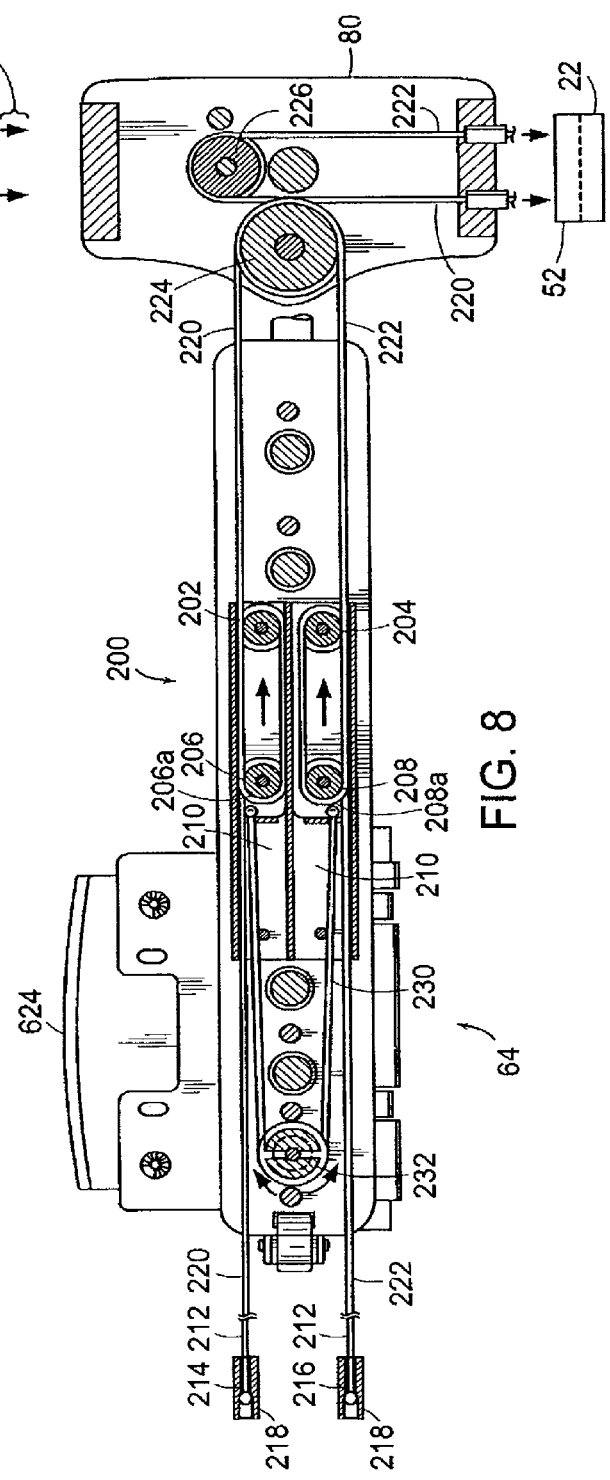

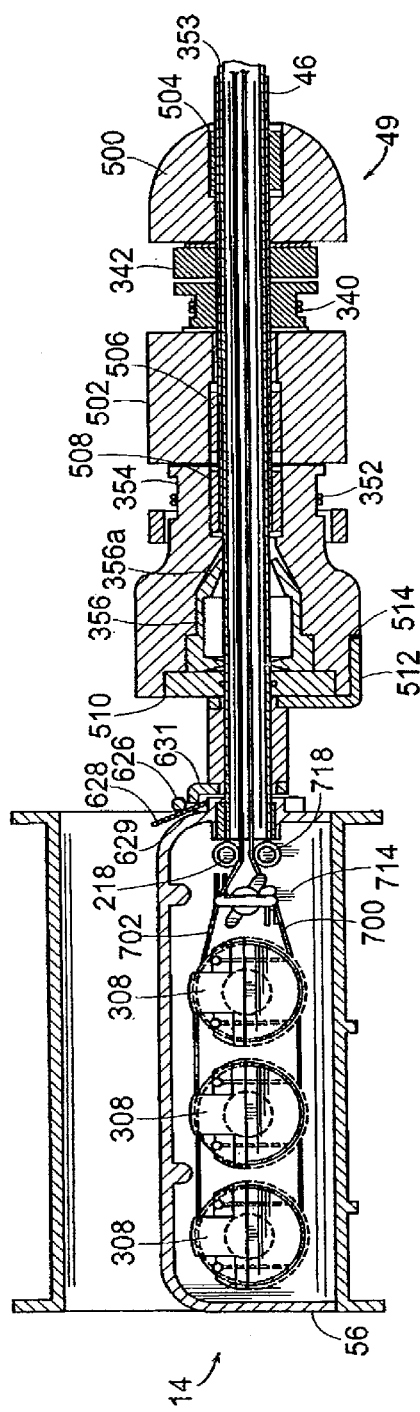
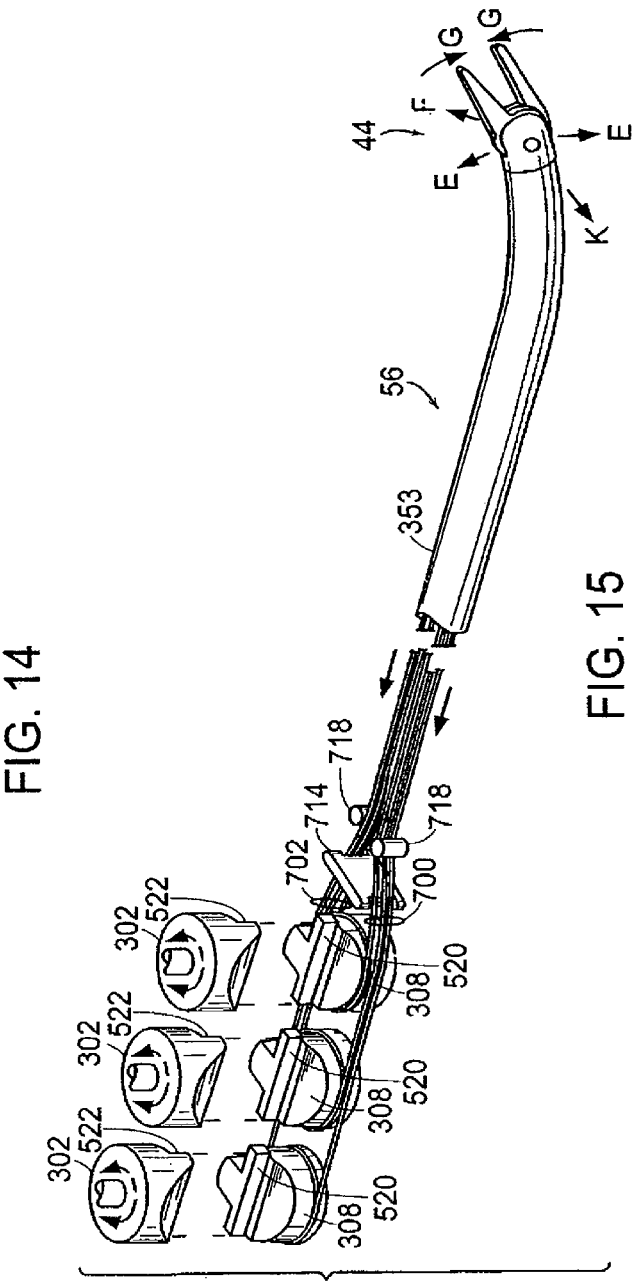

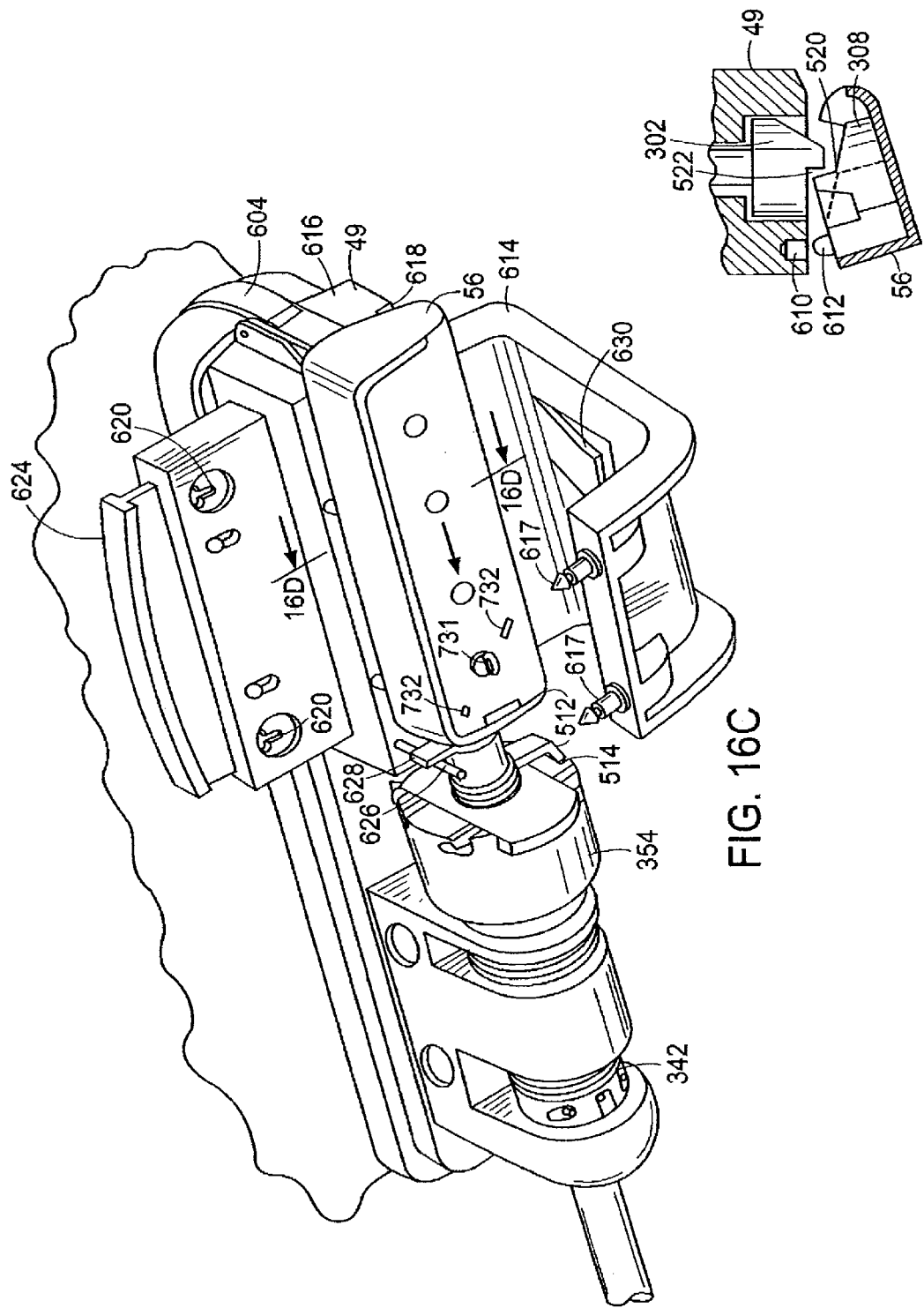

SURGICAL INSTRUMENT COUPLING MECHANISM

RELATED APPLICATIONS

This application is a continuation of U.S. application Ser. No. 10/302,804, filed Nov. 21, 2002, which claims benefit of priority from U.S. Application Ser. No. 60/409,530, filed Sep. 9, 2002. This application is also related to Application Ser. No. 11/762,743, filed on the same date herewith. The disclosures of these applications are expressly incorporated herein by reference.

BACKGROUND OF THE INVENTION

For certain medical procedures, minimally invasive surgery has replaced conventional surgery where the patient's body cavity is open to permit the surgeon's hands and instruments access to the cavity and internal organs. Minimally invasive procedures are typically less traumatic than conventional surgery, in part, because of the significant reduced incision size through which the medical instruments are inserted.

A video camera may be inserted into the patient in the area of the surgical site to view the procedure. It is, of course, important that the surgeon have some feedback either through a camera and fiber optic cable, or through real-time computerized tomography scan imagery. However, even with such visualization, the surgeon's tactile and position senses are physically removed from the operative site.

Some have proposed, therefore, the use of robots in surgery. Although current laparoscopy limits dexterity, and robotics restores dexterity, presently, existing systems, using manipulators both with and without haptic feedback, are generally too bulky and heavy for many minimally invasive procedures, or are too weak and imprecise for surgery.

SUMMARY OF THE INVENTION

In accordance with a first aspect of the present inventions, a medical system is provided. The medical system comprises a surgical instrument carrying a distal tool configured for performing a medical procedure on a patient. The medical system further comprises an adapter having a clam-shell configuration configured for removably receiving a proximal end of the surgical instrument. The medical system further comprises a drive unit (e.g., one having a motor array) configured for being coupled to the adapter to control the movement of the surgical instrument within at least one degree-of-freedom (e.g., an actuation of the distal tool). The drive unit may be coupled to the adapter via external cabling.

In one embodiment, the medical system further comprises a remote controller configured for directing the drive unit to control the movement of the surgical instrument within the degree(s)-of-freedom. The remote controller may have a user interface for receiving commands from a user. In this case, the movements made at the user interface may correspond to movements of the surgical instrument. The remote controller may be coupled to the drive unit via external cabling. In another embodiment, the medical system may further comprise a coupling mechanism through which the adapter is operably coupled to the drive unit. The coupling mechanism may comprise a carriage on which the surgical instrument is slidably mounted. In still another embodiment, the adapter has a driver element configured for being actuated by the drive unit, and the surgical instrument has a driven element configured for being actuated by the driver element to move the surgical instrument within the degree(s)-of-freedom. The driver element may be, e.g., a drive shaft, and the driven element may be, e.g., a wheel that mates with the drive shaft.

The clam-shell configuration of the adapter may be accomplished in any one of a variety of manners. For example, the adapter and the proximal end of the surgical instrument may have corresponding mechanisms that align with each other when the proximal end of the surgical instrument is received within the adapter. As another example, the adapter may have a base portion and a clam-shell that pivots relative to the base portion between a first position that encloses the proximal end of the surgical instrument within the adapter and a second position that allows the proximal end of the surgical instrument to be removed from the adapter. In this case, the adapter may have a catch mechanism configured for engaging the clam-shell in the first position, and a release mechanism configured for being actuated to disengage the clam-shell from the catch mechanism to place the clam-shell within the second position.

In accordance with a second aspect of the present inventions, a surgical instrument adapter is provided. The surgical instrument adapter comprises a base portion configured for receiving a proximal end of a surgical instrument, and a clam-shell that pivots relative to the base portion between a first position that encloses the proximal end of the surgical instrument within the base portion and a second position that allows the proximal end of the surgical instrument to be removed from the base portion. The surgical instrument adapter further comprises a driver element (e.g., a drive shaft) configured for actuating a driven element located at the proximal end of the surgical instrument to move the surgical instrument within at least one degree-of-freedom (e.g., an actuation of a distal tool carried by the medical instrument). In one embodiment, the driver element is configured for being actuating by a drive unit located external to the adapter. In another embodiment, the adapter has a mechanism configured for aligning the proximal end of the surgical instrument within the base portion. In still another embodiment, the adapter has a catch mechanism configured for engaging the clam-shell in the first position, and a release mechanism configured for being actuated to disengage the clam-shell from the catch mechanism to place the clam-shell in the second position.

BRIEF DESCRIPTION OF THE INVENTION

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 7 is cross-sectional view of a linear drive mechanism taken along the line 7-7 of FIG. 4.

FIG. 8 is a cross-sectional view of a block and tackle assembly taken along the line 8-8 of FIG. 4.

FIG. 14 is a cross-sectional view of an instrument insert and drive mechanism taken along the line 14-14 of FIG. 4.

FIG. 15 is a perspective view of an insert drive cabling of FIG. 14.

FIG. 16C is an exploded view of the instrument adapter and clamshell with the tool insert mostly inserted into the guide shaft.

FIG. 16D is a cross-sectional view taken along the line 16D-16D of FIG. 16C.

DETAILED DESCRIPTION OF THE INVENTION

A description of preferred embodiments of the invention follows.

Figure 1:
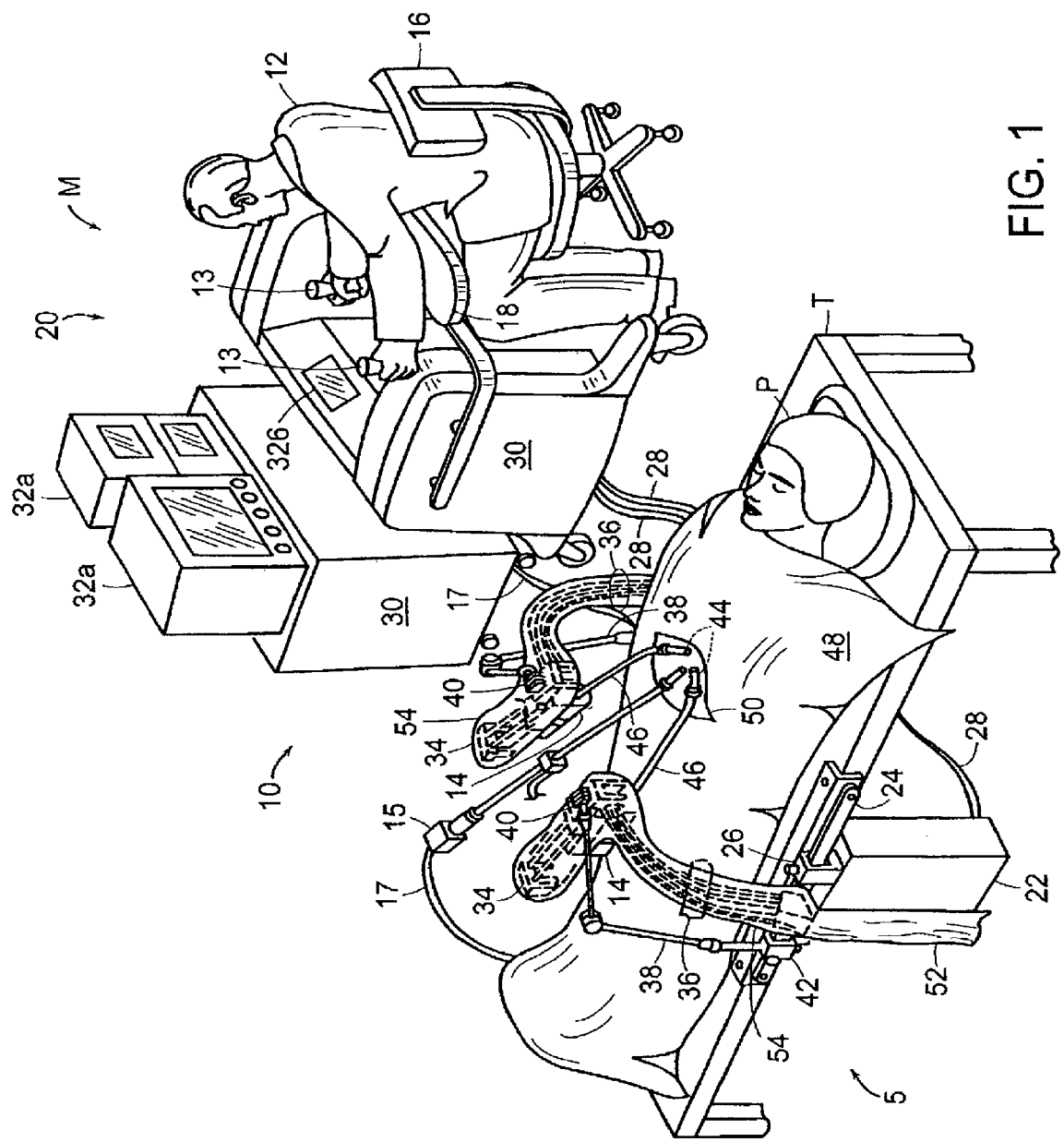
FIG. 1 is a perspective view of a telerobotic surgical system in accordance with the invention.

The surgical robotic system of the present invention, illustrated generally at 10 in FIG. 1, although preferably used to perform minimally invasive surgery, can also be used to perform other procedures as well, such as open or endoscopic surgical procedures. Certain details of the operation of the system 10 are described in U.S. application Ser. No. 10/014,143 filed Nov. 16, 2001, by Brock and Lee, the entire contents of which are incorporated herein by reference.

The surgical instrument system 10 includes two main components, a master station M and a slave station S. At the master station M, a surgeon 12 manipulates an input device 13 to direct the operation of a surgical instrument 14 of the slave station S to perform a medical procedure on a patient P lying on an operating table T. Although there are shown two surgical instruments 14 positioned on either side of an endoscope 15 and controlled by a respective input device 13, the surgical system 10 can be used with a single surgical instrument. Moreover, although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

The surgeon is illustrated as seated in a comfortable chair 16, and the forearms of the surgeon are typically resting upon an armrest 18 of a master assembly 20 associated with the master station M. A slave assembly 22, also referred to as a drive unit, is associated with the slave station S, and is attached to a rail 24 of the table T with a clamp 26, which can be released such that the drive unit can be optimally positioned. In some implementations, the master station M is positioned away from the slave station S, for example, in another room. The assemblies 20 and 22 are interconnected by a cabling 28 with a controller 30, which typically has associated with it one or more displays 32a for viewing the surgical site, and a display 32b for monitoring the system performance of the system 10, and a keyboard (not shown). A slider mechanism 34, which carries the medical instrument 14, is supported by a support arm 38. The drive unit 22 is tethered to the slider mechanism 34 with a bundle of mechanical drive cables 36. The support arm 38 is provided with a clamp 40 at one end that clamps to the slider mechanism, and another clamp 42 that clamps the support arm to the rail 24. This mounting arrangement permits the instrument to remain fixed relative to the patient even if the table is repositioned.

The master station M may also be referred to as a user interface vis-a-vis the controller 30. Associated with the controller 30 is a computer that operates in accordance with a computer algorithm, such that the computer translates the commands issued at the user interface into electronic signals transmitted to the drive unit 22 through the cabling 28. These signals direct the operation of the drive unit 22, which has motors to transform the electrical signals into mechanical movement of the cables 36 to produce the desired replicated motions of the surgical instrument 14. In particular, the movement of the handle or hand assembly at the input device 13 is interpreted by the controller 30 to control the movement of the medical instrument 14. The use of the cables 36 facilitates positioning of the drive unit 22 away from the operation region, for example, from the sterile field.

Figure 2:
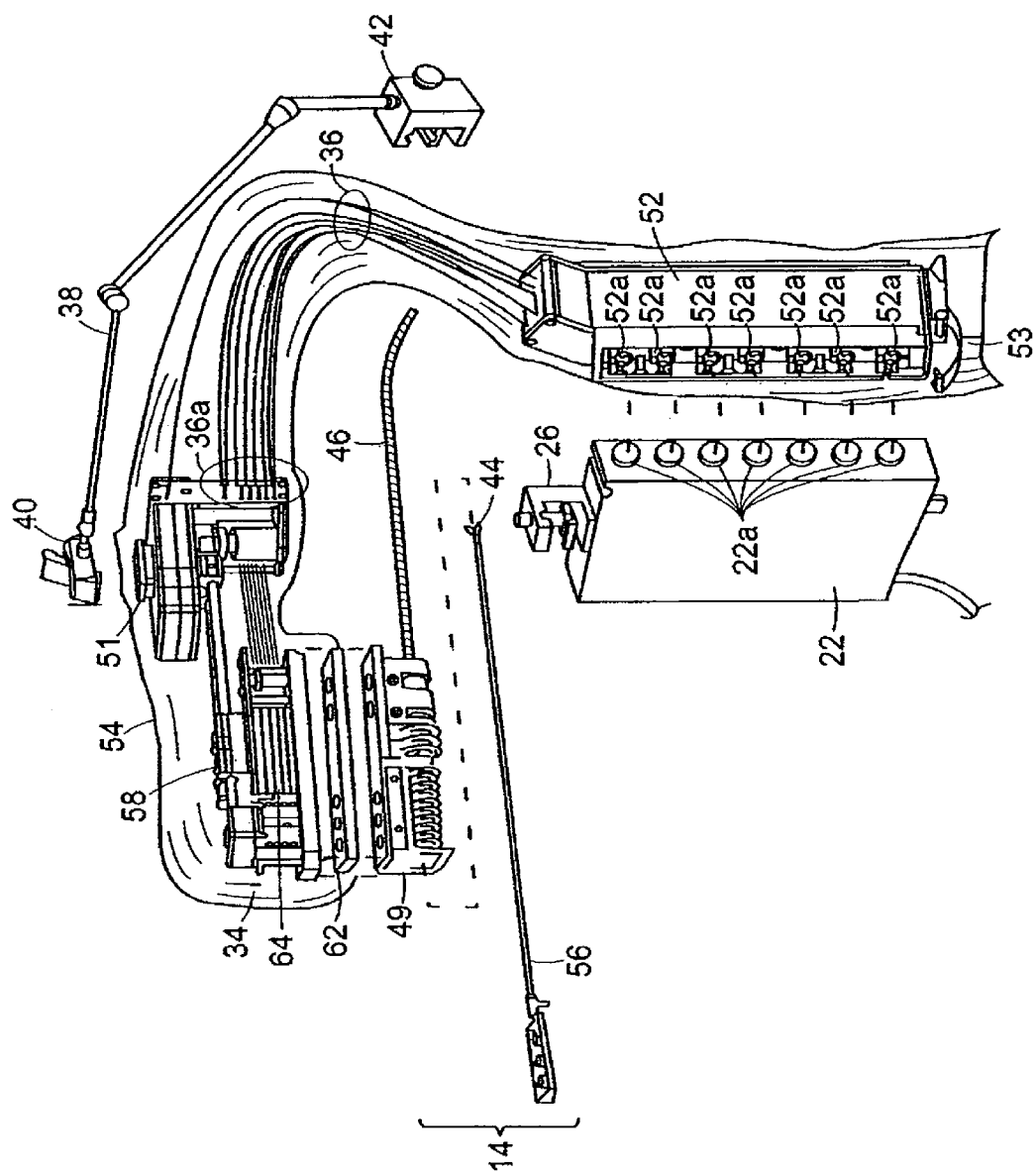
FIG. 2 is a close-up view of a slider and drive mechanism of the system of FIG. 1.

In the illustrated embodiment, the surgical instrument 14 includes an instrument insert 56 that supports, at its distal end, a tool 44, and an adaptor 49, also referred to as a holder, having a guide tube 46 that receives the instrument insert 56 (FIG. 2). The surgical instrument 14 is coupled to a coupling mechanism, preferable a slider mechanism 34. In this implementation, the surgical instrument 14 provides a number of independent motions, or degrees-of-freedom, to the tool 44. The surgical guide 46 is basically a passive mechanical device and may be of relatively simple construction. It is a simple guide tube, curved at its distal end, through which the end effector or tool 44 is inserted. Motion of the guide tube results in a movement of the end effector or tool 44. The guide tube may be designed in length, diameter, and curvature for particular surgical applications such as abdominal, cardiac, spinal, arthroscopic, sinus, neural, etc. The adaptor 49 provides a means for exchanging the instrument inserts and thus the instrument tools 44, which may be, for example, forceps, scissors, needle drivers, electrocautery probes etc.

The endoscope 15 (FIG. 1) includes a camera to remotely view the operation site. The camera may be mounted on the distal end of the instrument insert, or may be positioned away from the site to provide an additional perspective on the surgical operation. In certain situations, as shown, it may be desirable to provide the endoscope through an opening other than the one used by the surgical instrument 14. The endoscope 15 is connected to the master station M with a cable 17 to allow the surgeon 12 to view the procedure with the monitors 32a.

In this regard, three separate incisions are shown in the patient P, two side incisions for accommodating the two surgical instruments 14 and a central incision that accommodates the viewing endoscope. A drape 48 covering the patient is also shown with a single opening 50 through which the surgical guide 46 of the surgical instrument 14 extends into the patient P.

The cable bundles 36 may terminate at respective connection modules or drive unit couplers 52, which attach to and may be removed from the drive unit 22. Further details of the connection modules 52 can be found in the earlier co-pending applications No. PCT/US00/12553 and U.S. application Ser. No. 10/014,143 filed Nov. 16, 2001, the entire contents of which are incorporated herein by reference. Although one cable bundle is shown associated with each of the surgical instruments 14, it is to be understood that more than one cable bundle can be used. Furthermore, although the drive unit 22 is shown located outside the sterile field, it may be draped with a sterile barrier so that it can be operated within the sterile field.

To set up the system 10, the user connects the drive unit couplers 52 to the drive units 22 and places a sterile drape 54 over slider mechanisms 34, cable bundle 36 and the drive unit couplers 52. The user then clamps the support arm 38 to the slider mechanism 34 with the clamp 40, which clamps a knob 51 through the drape 54. The user attaches the sterile adaptor 49 to the underside of the slider mechanism 34 such that the drape 54 is positioned between the slider mechanism 34 and the adaptor 49. The user then places a sterile tool insert 56 (see, e.g., FIG. 2) into the adaptor 49 such that the tool 44 extends past the terminal end of the guide tube 46, and inserts the tool 44 of the surgical instrument 14 into the patient through the incision or opening.

Particular details of the system 10 and its operation are now described below with reference to FIGS. 2-18.

Turning to FIG. 2, the surgical instrument 14 is coupled to a carriage 58 of the slider mechanism 34 with the insert adaptor 49 through a sterile drape insert 62. The sterile drape insert 62 is attached to the drape 54 in a manner to create a sterile field outside of the drape 54. The drape 54 is typically made of a suitable flexible material, while the drape insert 62 is made of metal or a stiff plastic. The drive unit 22 includes a set of motors (seven total) with capstans 22a that engage with respective drivers 52a of the drive coupler 52.

FIG. 2 also shows how the slider mechanism 34 is connected to the drive coupler 52 with the single bundle of cables 36. In particular, the control wires or cables of the bundle 36 connect to the slider mechanism 34 at a single location 36a that does not move. That is, although the cables within the bundle 36 weave through the slider mechanism 34, and are coupled to respective driven capstans or drive pulleys, the point of attachment 36a to the slider mechanism 34 is stationary. Hence, none of the cables interferes with the movement of the slider mechanism and thus the surgical instrument and vice versa. It is not necessary for the bundle 36 to be composed of cables. Any suitable flexible segment or tendon can be used in place of one or more of the cables in the bundle 36.

Figure 3:
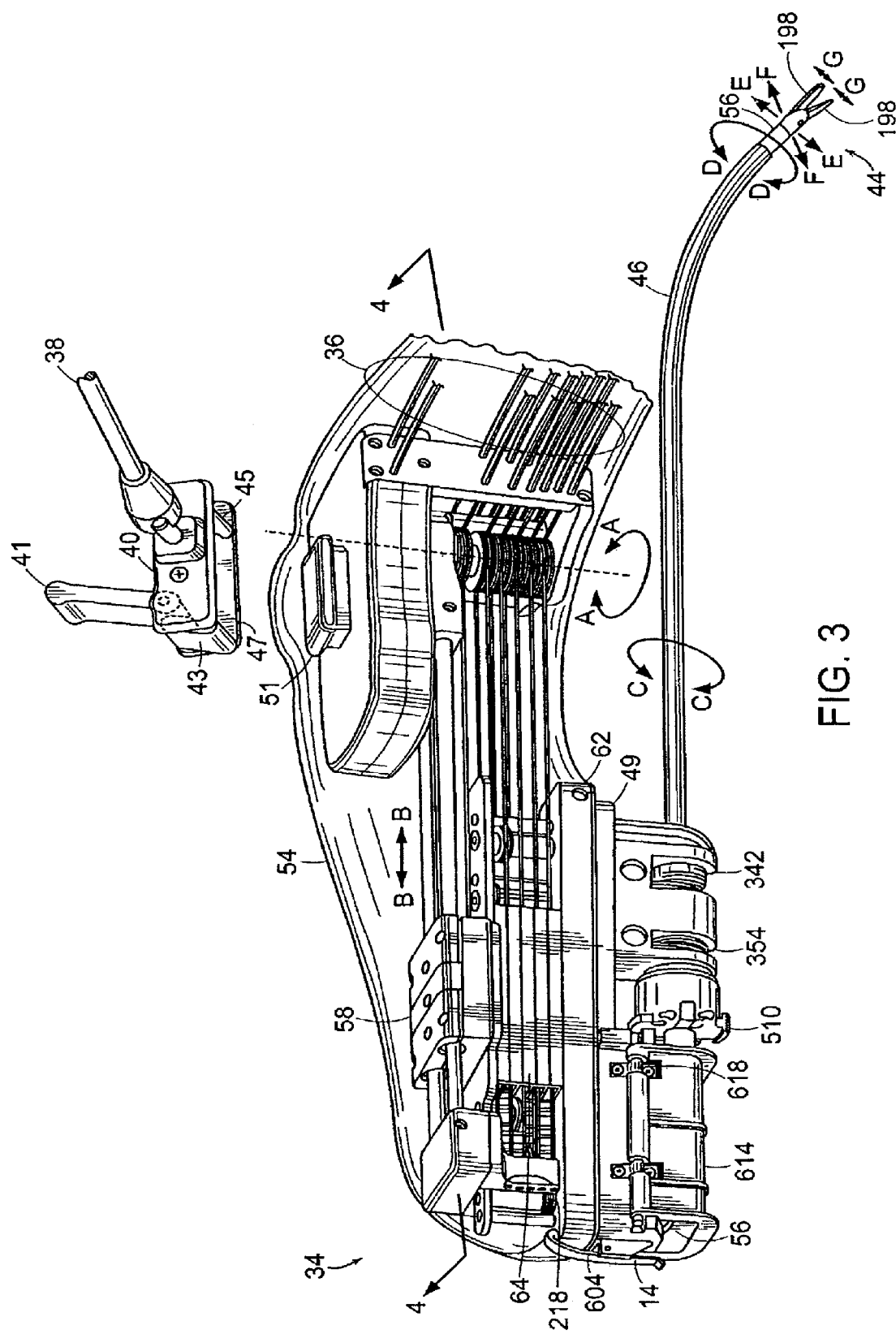
FIG. 3 is close-up view of the slider mechanism of FIG. 2.

Referring also to FIG. 3, the carriage 58 includes a block and tackle assembly 64 that decouples the movements of the guide tube 46 and the tool 44 from the overall linear (B-B) and angular (A-A) movements of the slider mechanism 34. Thus, as the surgeon 12 manipulates the input device 13 (FIG. 1), the computer system 30 issues commands to the drive motor array 22 to produce a desired motion of the instrument 14. In the illustrated embodiment, the surgical instrument 14 is able to move with seven degrees-of-freedom: the pivoting base motion A-A of the slider mechanism 34, and thus the carriage 58, the linear motion B-B of the carriage 58, a rotary motion C-C of the outer guide tube 46, a rotary motion D-D of the tool insert 56, a pitch E-E motion and a yaw F-F motion of the tool 44, and a grasping motion G-G of a pair of graspers 198 of the tool 44. Each movement is driven from a respective motor capstan 22a of the drive unit or array 22 through push/pull wires or cables of the bundle of cables 36 coupled to the slider mechanism 34.

FIG. 3 also illustrates details of the clamp 40 which includes a handle 41, a moveable jaw 43, and a stationary jaw 45, all mounted in a housing 47. The handle 41 and the jaw 43 function as a cam action lock so that as someone pushes the handle 41 down towards the housing 47, the moveable jaw 47 and the stationary jaw 45 lock onto the knob 51 at the top of the slider mechanism 34 to secure the slider mechanism 34 to the support arm 38.

Figure 4:
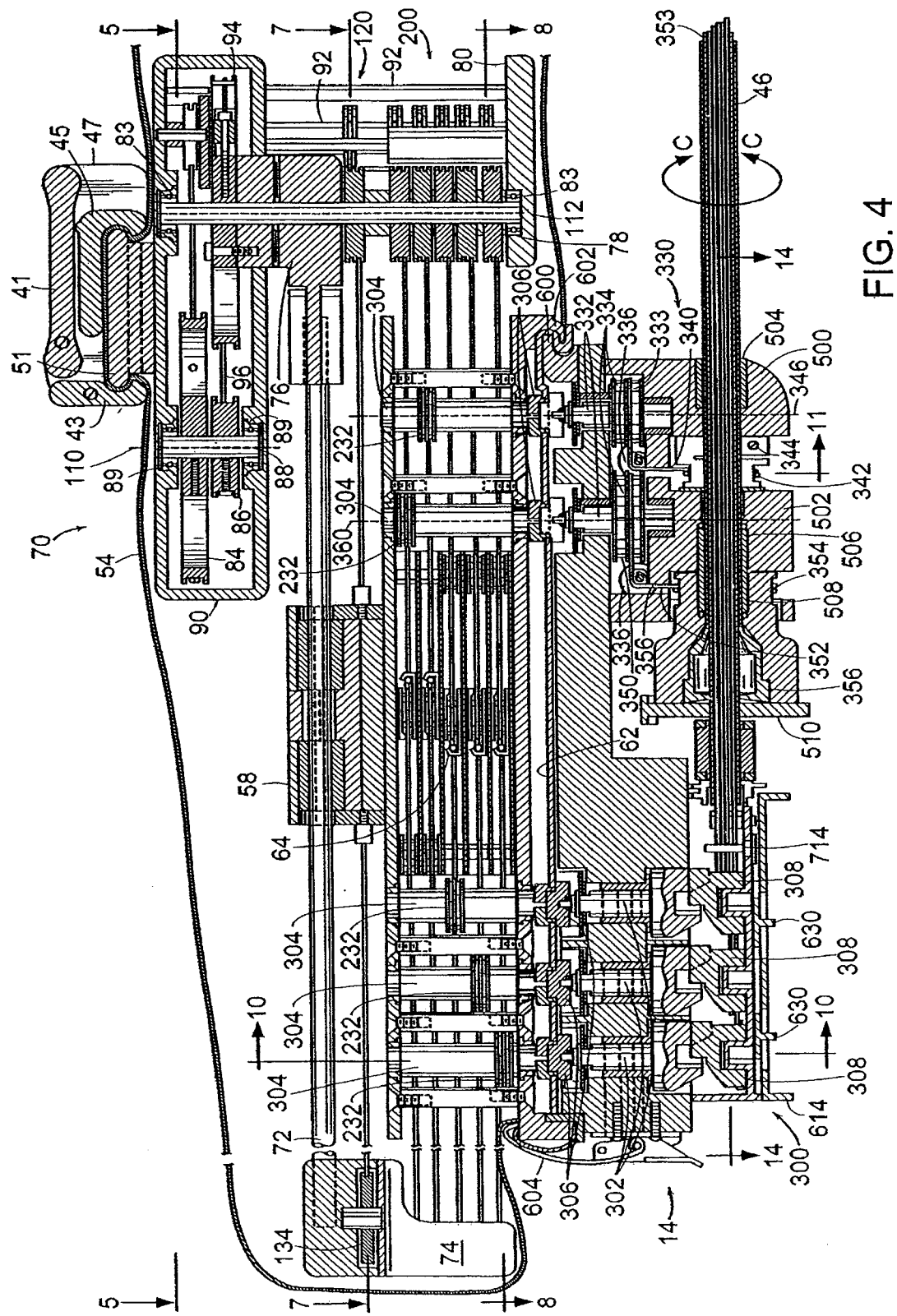
FIG. 4 is a cross-sectional view of the slider mechanism taken along the line 4-4 of FIG. 3 with a support clamp attached to the slider.
Figure 5:
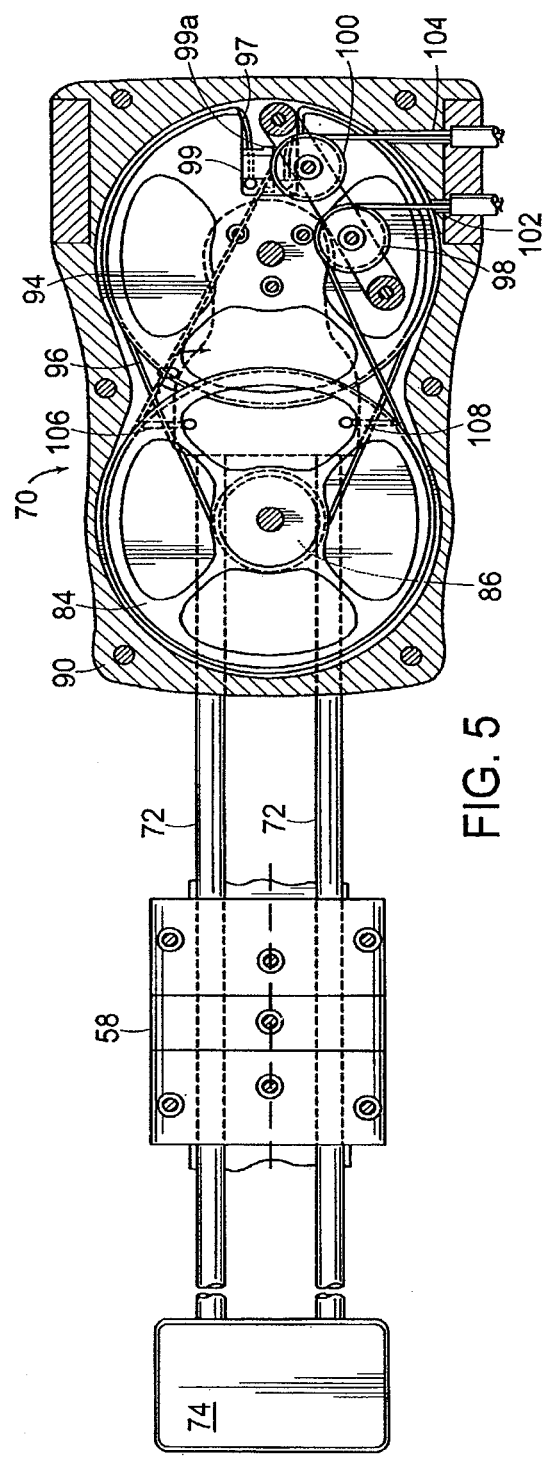
FIG. 5 is a cross-sectional view of an angle drive mechanism taken along the line 5-5 of FIG. 4.
Figure 6:
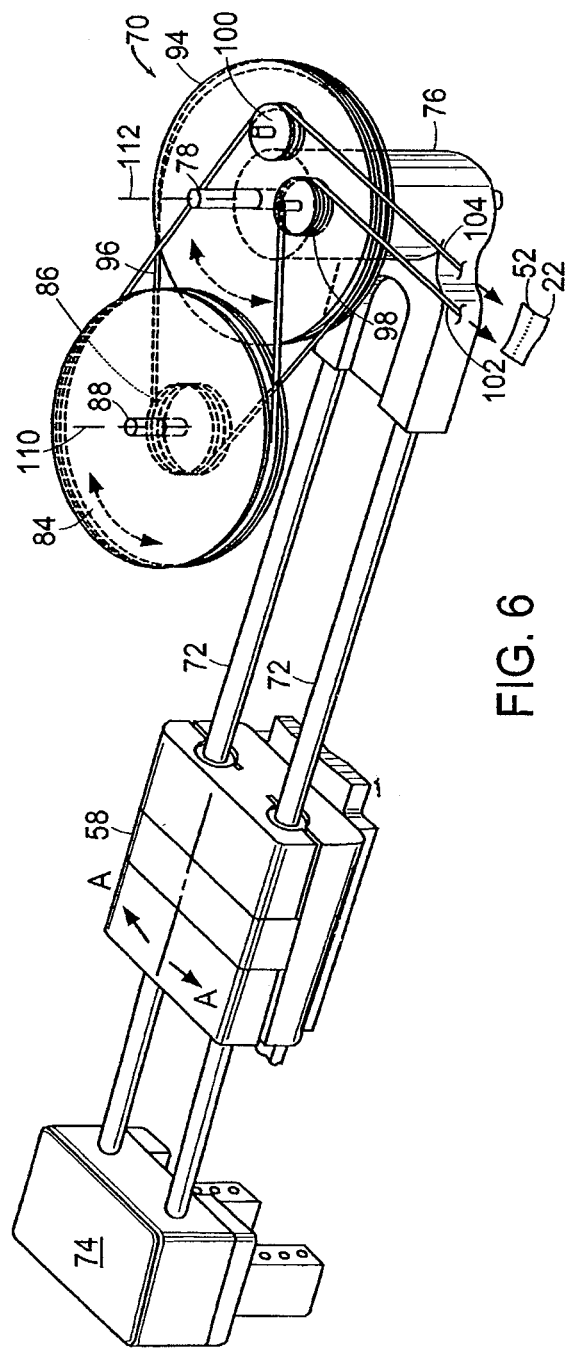
FIG. 6 is a perspective view of the angle drive mechanism of FIG. 5.

Turning now to FIGS. 4-6, there is shown the carriage 58 supported by a pair of rails 72 attached at one end to an end block 74, and at the other end to a rotatable base 76. The rotatable base 76 is connected to an axle 78 which in turn is mounted to an end cap 80 and a housing 90 with a pair of bearings 83. The end cap 80 is suspended from the housing 90 by a set of bars 92. An angle drive mechanism 70 includes a pair of gear reduction pulleys 84 and 86 connected to another axle 88 mounted with a pair of bearings 89 to the housing 90. The drive mechanism 70 also includes a driven pulley 94 secured to the axle 78, and coupled to the gear reduction pulley 86 with a cable 96. As shown in FIG. 5, the cable 96 has two ends 97 that attach to a cable tensioning block 99 mounted in the driven pulley 94. Thus, as a set screw 99a is turned, thereby moving the block 99, the appropriate tension is applied to the cable 96. A pair of cable segments 102 and 104 of the bundle of cables 36 are guided through a pair of guide pulleys 98 and 100 and attach to the gear reduction pulley 84 with respective cable anchors 106 and 108. The other ends of the cables 102 and 104 are coupled to respective motor capstans 22a of the drive unit 22 through the drive coupler 52.

Accordingly, as a motor of the drive unit 22 applies tension to either of the cables 102 or 104, a rotary motion is imparted to the pulley 84 and hence the pulley 86 about the longitudinal axis 110 of the axle 88. The rotary motion of the pulley 86 consequently imparts a rotary motion through the cable 96 to the driven pulley 94 about the longitudinal axis 112 of the axle 78. The driven pulley 94 in turn imparts a rotary motion of the rotatable base 76 and thus the carriage 58 back and forth in the direction of the double arrow A-A. Referring to FIG. 7, there is shown a linear drive mechanism 120 that moves the carriage 58 back and forth along the rails 72 in the direction B-B. The linear drive mechanism 120 includes a pair of cable segments 122 and 124 attached to the carriage with respective anchors 126 and 128. The cable 122 is guided about a guide pulley 130, while the cable 124 is guided through a guide pulley 132, the guide pulley 130, and about an idler pulley 134 mounted in the end block 74. The other ends of the cables 122 and 124 are attached to a motor of the drive unit 22 through the coupler 52. Accordingly, as tension is applied to the cable 122, the carriage moves from left to right, while tension applied to the cable 124 moves the carriage 58 from right to left.

Turning now to FIG. 8, there is shown details of the block and tackle assembly 64. The block and tackle assembly 64 includes a coupling system 200 for each of the degrees-of-freedom C-C, D-D, E-E, F-F, and G-G (FIG. 3) that are decoupled from the linear B-B and rotary movements A-A of the carriage 58. Although the coupling systems 200 are layered or stacked, the operation of the systems is best illustrated with reference to the single coupling system shown in FIG. 8 and further illustrated in FIGS. 9A-9E. The coupling system 200 includes two stationary pulleys 202 and 204 fixed to the slider 58, and two additional pulleys 206 and 208 mounted in respective sliders 206a and 208a that are able to slide relative to the carriage 58 along tracks 210. The pulleys 202, 204, 206, and 208 and the sliders 206a and 206b are made of plastic or metal, and the tracks 210 are formed of plastic or Teflon.™ or any other suitable material that minimizes friction between the tracks 210 and the sliders 206a and 206b. A pair of cable segments 220 and 222 are attached at a first location 214 and a second location 216, respectively, to a pair of anchors 218 on the end block 74. The first cable segment 220 wraps around the sliding pulleys 206 and the stationary pulley 202, and the second cable segment 222 wraps around the other sliding pulley 208 and the other stationary pulley 204. The two segments 220 and 222 are fed through a pair of guide pulleys 224 and 226 and are coupled to a respective motor of the array 22 through the coupler 52. The sliding pulleys 206 and 208 are also connected with another cable 230 to a driven capstan 232 that imparts one of the degrees-of-freedom of movement C-C, D-D, E-E, F-F, and G-G (FIG. 3) to the surgical instrument.

When the system 10 is in operation, as the carriage 58 moves back and forth with the linear motion B-B (FIG. 9E), the cable segments 220 and 222 roll freely over the pulleys 202, 204, 206, and 208 without rotating the driven capstan 232. That is, the linear movement of the carriage 58 does not influence, and is therefore decoupled from, the degrees-of-freedom of movement C-C, D-D, E-E, F-F, and G-G.

Figure 9A:
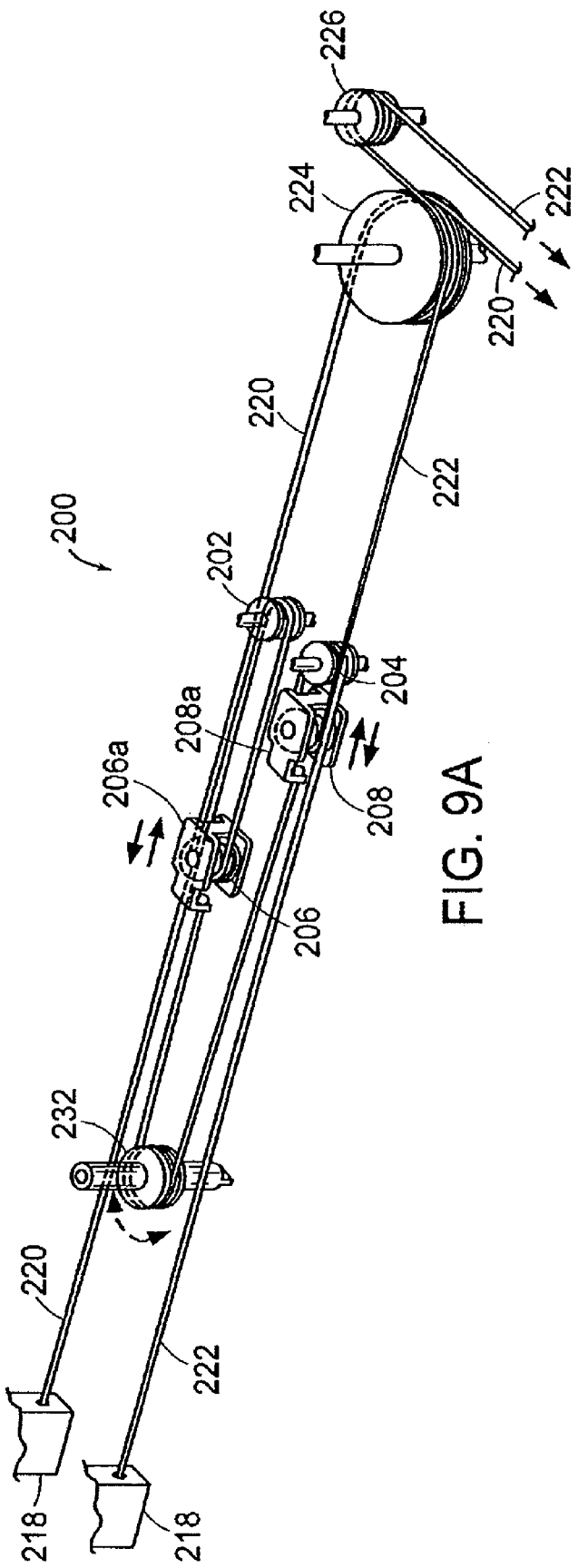
FIG. 9A is a perspective view of the block and tackle assembly of FIG. 8.
Figure 9B:
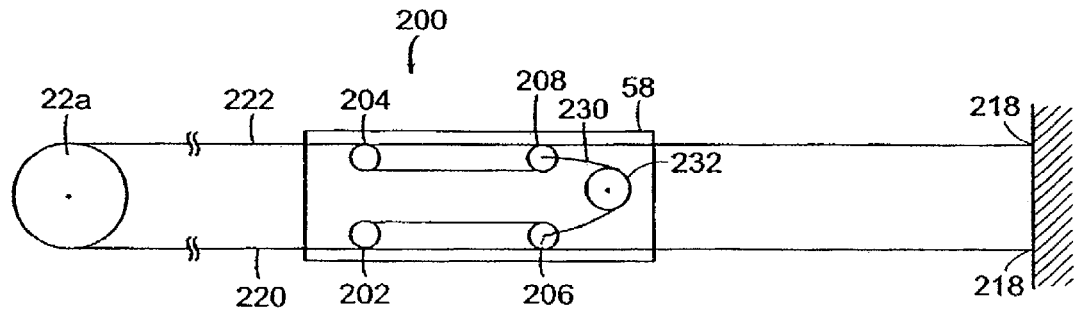
FIGS. 9B-9E illustrate a sequence of steps for operating the block and tackle assembly of FIG. 8.
Figure 9C:
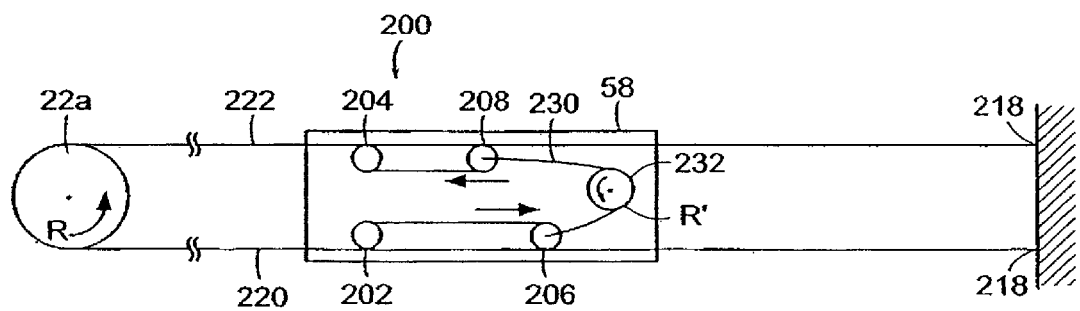

If, however, the capstan 22a is rotated to pull on the segment 220 or segment 222, the distance between one of the stationary pulleys 202 or 204 and the corresponding sliding pulley 206 or 208 decreases, while the distance between the other fixed and sliding pulleys increases, resulting in a rotary motion of the driven capstan 232. By way of example, as shown in FIG. 9C, if the capstan 22a is rotated counterclockwise in the direction R to pull on the cable segment 222 from an initial position shown in FIG. 9B, the length of the cable 222 around the pulleys to the anchor 218 is shortened, causing the sliding pulley 208 to move towards the stationary pulley 204. Since the cable 230 is of a fixed length, it pulls the other sliding pulley 206 away from the stationary pulley 202, and rotates the driven capstan 232 counterclockwise with a rotary movement R'. No linear movement is imparted to the carriage 58.

Figure 9D:
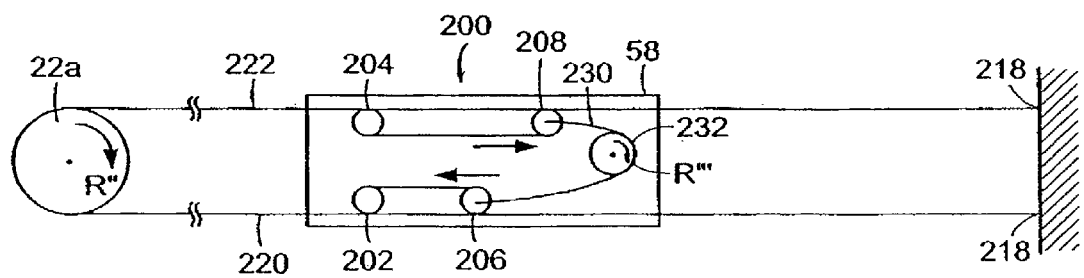
Figure 9E:
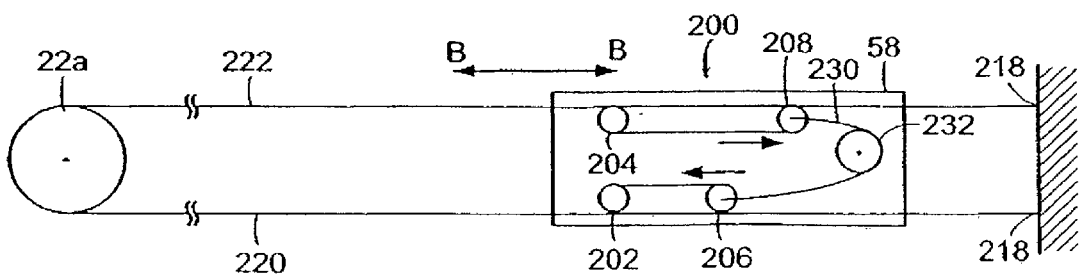

Similarly, as shown in FIG. 9D, if the capstan 22a is rotated clockwise in the direction R" to pull on the cable segment 220, the sliding pulley 206 moves towards the stationary pulley 202, while the sliding pulley 208 moves away the stationary pulley 204, which imparts a clockwise rotary motion R''' to the driven capstan 232.

Note, as mentioned earlier, the movements B-B, C-C, D-D, E-E, F-F, and G-G do not influence and are therefore decoupled from the rotary movement A-A of the carriage 58.

Figure 10:
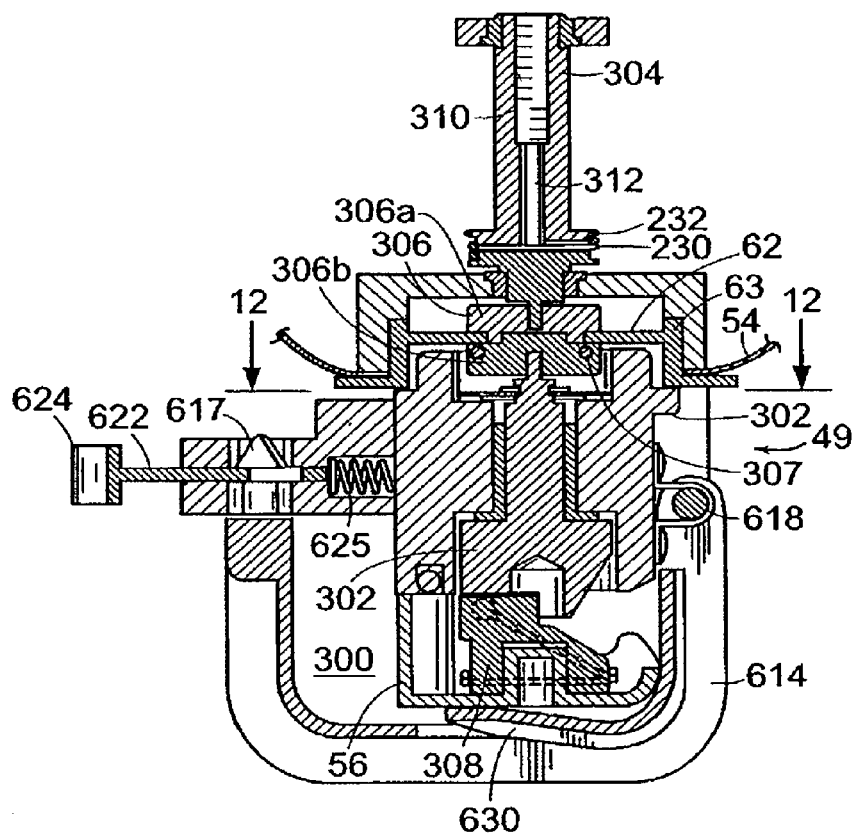
FIG. 10 is a cross-sectional view of a split drive shaft taken along the line 10-10 of FIG. 4.
Figure 11:
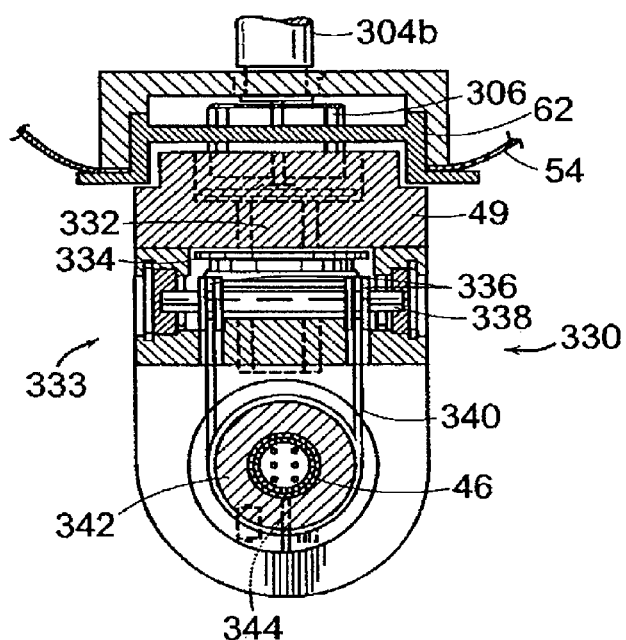
FIG. 11 is a cross-sectional view of a cable drive for an outer guide tube taken along the line 11-11 of FIG. 4.

Referring now to FIG. 10, a drive mechanism 300 used to drive one of the degrees-of-freedom E-E, F-F, or G-G of the tool 44 is shown. The drive mechanism 300 includes a lower drive shaft 302 mounted in the adapter 49. The lower drive shaft 302 is coupled to an upper drive shaft 304 of the coupling system 200 through a rotatable coupler 306 that is mounted in the drape insert 62. The lower drive shaft 302 is also coupled to a respective drive wheel 308 of the instrument insert 56. The upper drive shaft 304 is provided with a set screw 310 that when rotated pushes against a set screw extension 312 which clamps the cable 230 in the driven capstan 232 mounted about the upper drive shaft 304. As such, as the driven capstan 232 rotates, as discussed with reference to FIGS. 9A-9E, the rotary motion of the capstan 232 imparts a rotary motion of the drive wheel 308 through drive shaft 304, coupler 306, and the lower drive shaft 302.

As mentioned above, the insert can be made of a stiff plastic. Similarly, the coupler 306 can be made from two plastic pieces 306a and 306b (FIG. 10) connected together through a hole in the base 63 of the insert 62. The lower piece 306b is provided with a bearing 307 that allows the coupler 306 to rotate relative to the base 63. Either or both of the insert 62 and the coupler 306 can be made of metal rather than plastic.

Rotary motion of the guide tube 46 (C-C) and the insert 56 (D-D) are imparted though somewhat different mechanisms. In particular, referring to FIG. 11, a drive mechanism 330 used to drive the rotary motion of the outer guide tube 46 includes a lower drive shaft 332 mounted in the adapter 49. The lower drive shaft 332 is coupled to a respective upper drive shaft 304 through the coupler 306, similar to that described above for the lower drive shaft 302. However, unlike the previously described drive mechanisms 300, the lower drive shaft 332 is provided with a right angle cable drive 333. The cable drive 333 includes a pulley 334, and a pair of idler pulleys 336 mounted to the adapter 49 with a shaft 338 and positioned at 90.degree. from the pulley 334. A cable 340 is wrapped around the pulley 334, guided through the idler pulleys 336, and attached to an outer tube drive pulley 342 clamped to the outer guide tube 46 with a clamp screw 344. Hence rotary motion of the upper drive shaft 304 about an axis 346 (FIG. 4) results in a rotary motion (C-C) about an axis aligned at a 90.degree. angle from the axis 346.

Referring back to FIG. 4, a similar drive mechanism 350 is used to rotate the shaft 353 of the insert 56 in the direction D-D (FIG. 3). For the drive mechanism 350, a drive cable 352 is coupled to tool shaft drive pulley 354. The drive pulley 354 in turn is coupled to the shaft 353. As such, as the upper drive shaft 304 rotates about an axis 360, a consequent rotary motion is imparted to the shaft 353 to produce the rotary motion D-D.

Figure 12:
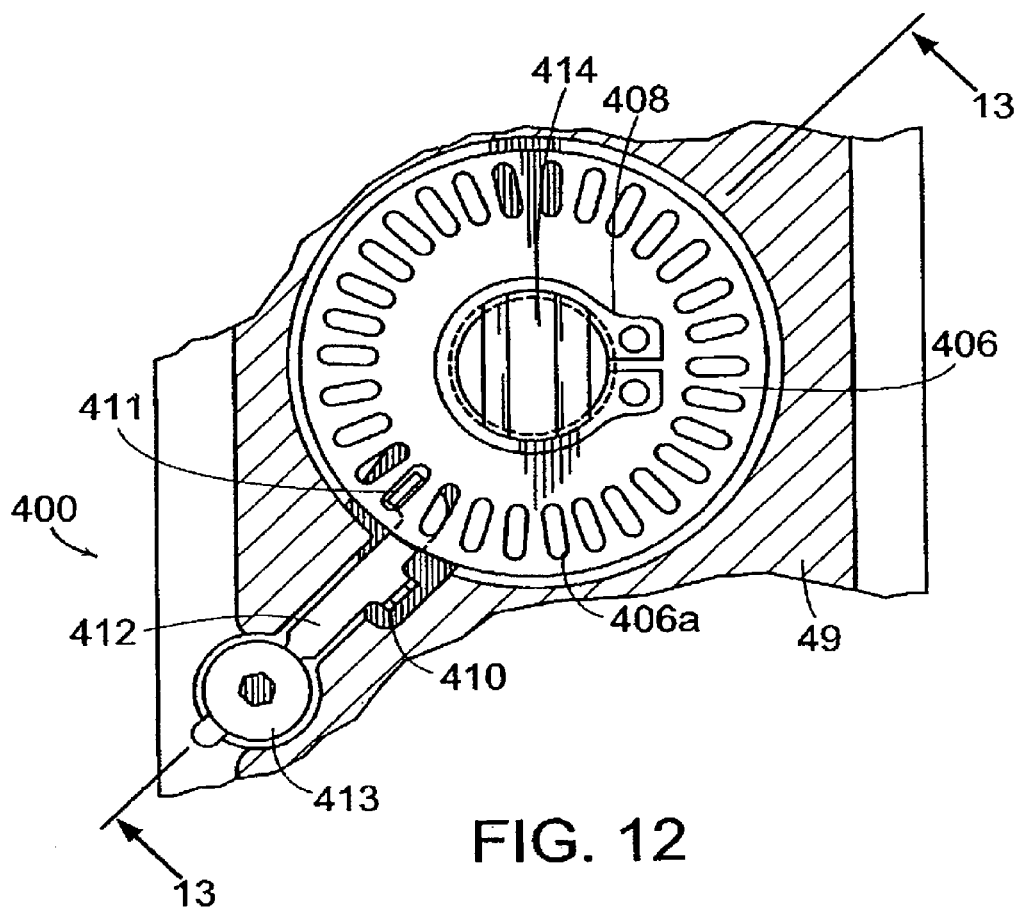
FIG. 12 is a fragmentary cross-sectional view of a drive shaft lockout mechanism taken along the line 12-12 of FIG. 10.
Figure 13:
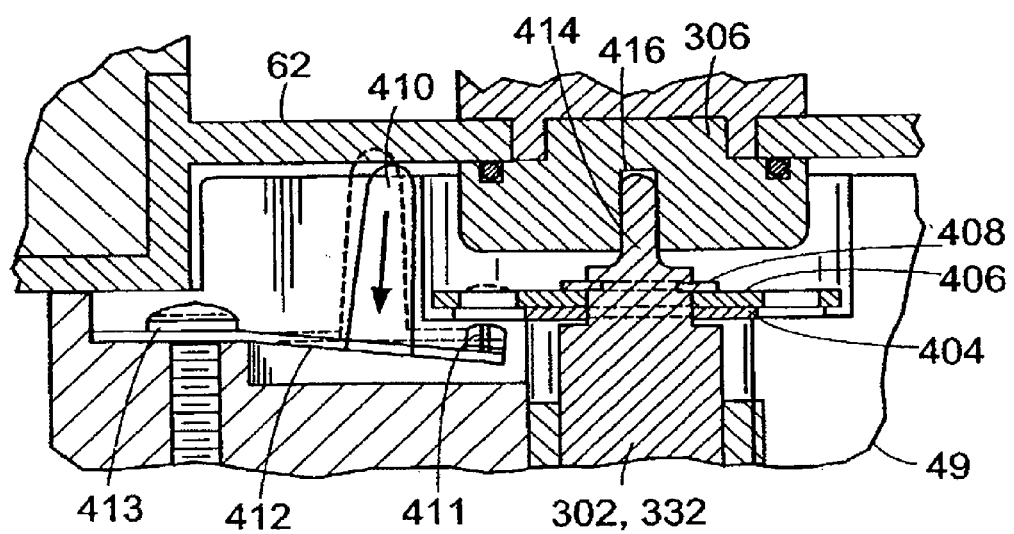
FIG. 13 is a cross-sectional view of a lockout disk mechanism taken along the line 13-13 of FIG. 12.

Referring to FIGS. 12 and 13, when the adaptor 49 is clamped to the drape insert 62, a blade like tip 414 of the adaptor 49 fits in a slot 416 of the coupling 306, so that rotation of the coupling 306 rotates the lower drive shaft 302 or 332. When removing the adaptor 49, a lockout mechanism 400 assures that the blade 414 remains in the same position to fit into the slot 416 when the adaptor 49 is reattached to the insert 62. That is, the lockout mechanism 400 prevents rotation of the lower drive shafts 302 or 332 when the insert adapter 49 and the drape insert 62 are not clamped together. The lower drive shaft 302 or 332 is provided with a washer 404 positioned beneath a disk 406. A clip 408 secures the washer 404, disk 406 and hence the lower drive shaft 302 in place. When the adapter 49 and the insert 62 are clamped together, a protrusion 410 on a flexure 412, attached to the surface the adaptor 49 with a screw 413, is pushed down by the drape insert 62 to release a catch tab 411 on the flexure 412 from engagement with the disk 406, thereby allowing the drive shaft to rotate. That is, the catch tab 411 is pushed out of a respective perforation or hole 406a of the disk 406. Meanwhile coupling between the lower drive shaft 302 and the coupler 306 occurs as the blade 414 engages with the slot 416 of the coupling 306.

Additional details of the arrangement of the outer tube drive pulley 342 and the shaft drive pulley 354 in relation to the insert 56 are shown in FIG. 14. The outer tube drive pulley 342 is positioned between an end section 500 and a mid section 502 of the adapter 49. As mentioned above the outer tube drive pulley 342 is clamped to the outer tube 46, which is mounted in the end section 500 and the mid section 502 with respective bearings 504 and 506. Hence rotation of the drive pulley 342 causes a consequent rotation of the guide tube 46 with the degree-of-freedom of movement C-C (FIG. 3). The shaft drive pulley 354 is positioned adjacent to the mid section 502 and mounted about the outer tube 46 with a bearing 508 so that it can rotate relative to the outer tube 46. A retainer clip 510 holds the drive shaft pulley 354 in place. The shaft pulley 354 is also provided with a valve 356, made from, for example, silicone. The shaft 353 is inserted through a flexible flap 356a with a hole in it and into the guide tube 46. Prior to the insertion of the shaft 353 into the guide tube 46, the resiliency of the valve 356 and in particular the flap 356a causes the hole in the flap to close off, hence, creating a seal between the guide tube 46 and the remainder of the adaptor 49 to prevent gas from escaping from the operating site through the guide tube 46. Similarly, when the shaft 353 is in place, the flap 356a forms a seal about the shaft 353 to prevent the escape of gas. A drive arm 512 of the insert 56 engages with a slot 514 of the pulley 354 to couple the shaft 353 with the pulley 354 so that the shaft 353 rotates with the pulley 354 with the degree-of-freedom of movement D-D (FIG. 3).

Referring now to FIG. 15, there is illustrated how the drive wheels 308 of the insert 56 engage with respective lower drive shafts 302. In particular, a face 520 of each drive wheel 308 mates with an opposing face 522 of the respective lower drive shaft 302.

Figure 16A:
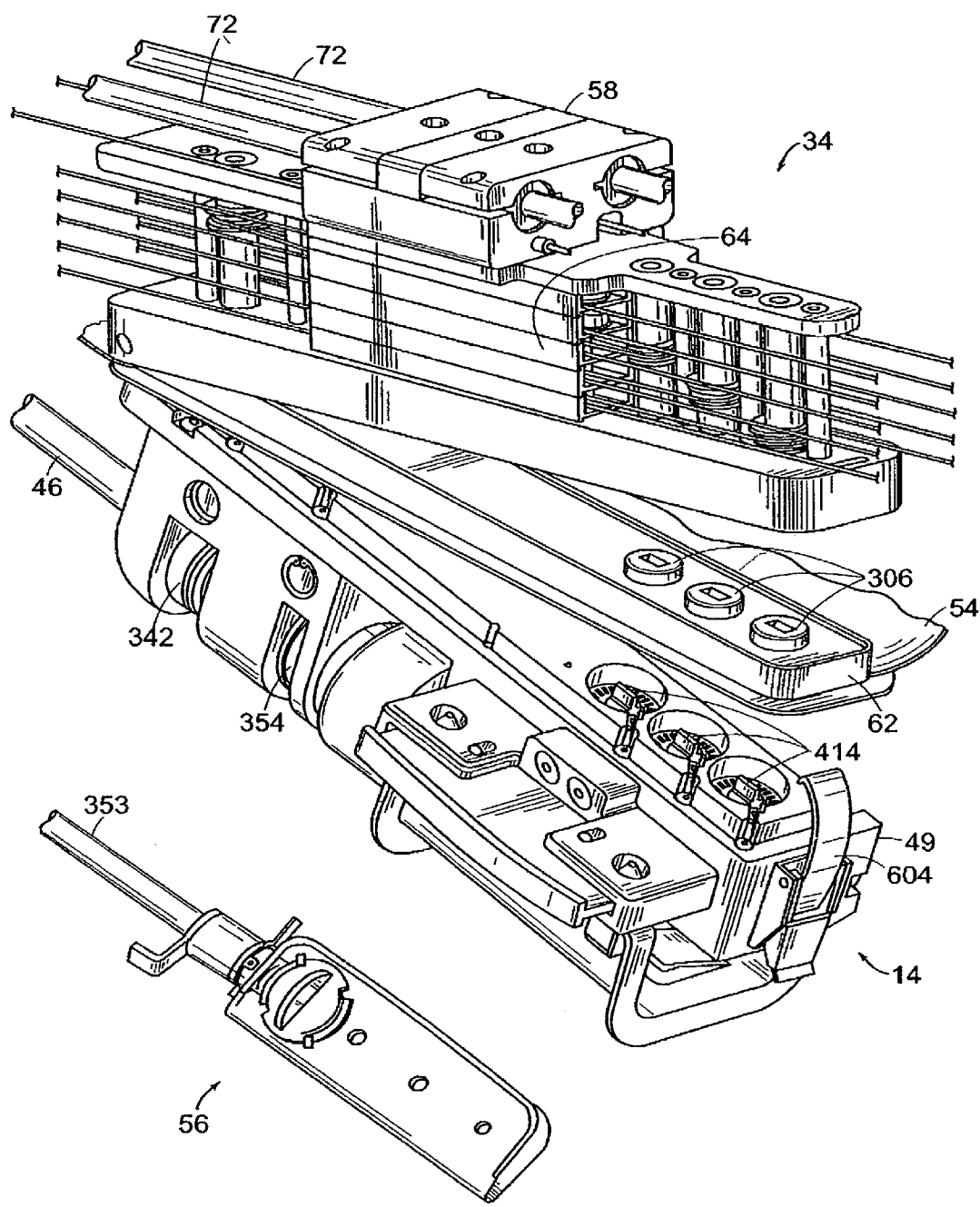
FIG. 16A is an exploded view of a partially disassembled slider unit.

Referring now to FIG. 16A, as well as FIGS. 2 and 4, details of the attachment of the adaptor 49 to the slider mechanism 34 are shown, as well as the insert 56 prior to insertion of the shaft 353 into the guide tube 46. The drape 54 is placed between the adaptor 49 and the bottom of the carriage 58, and then a lip 600 of the adaptor 49 is placed into a corresponding lip 602 of the carriage assembly 58, with the drape 54 pinched between the two lips. The adaptor 49 is then rotated up so that it engages with the carriage 58 through the drape insert 62. A clamp 604 is then snapped in place to secure the adaptor 49 to the slider mechanism 34.

Figure 16B:
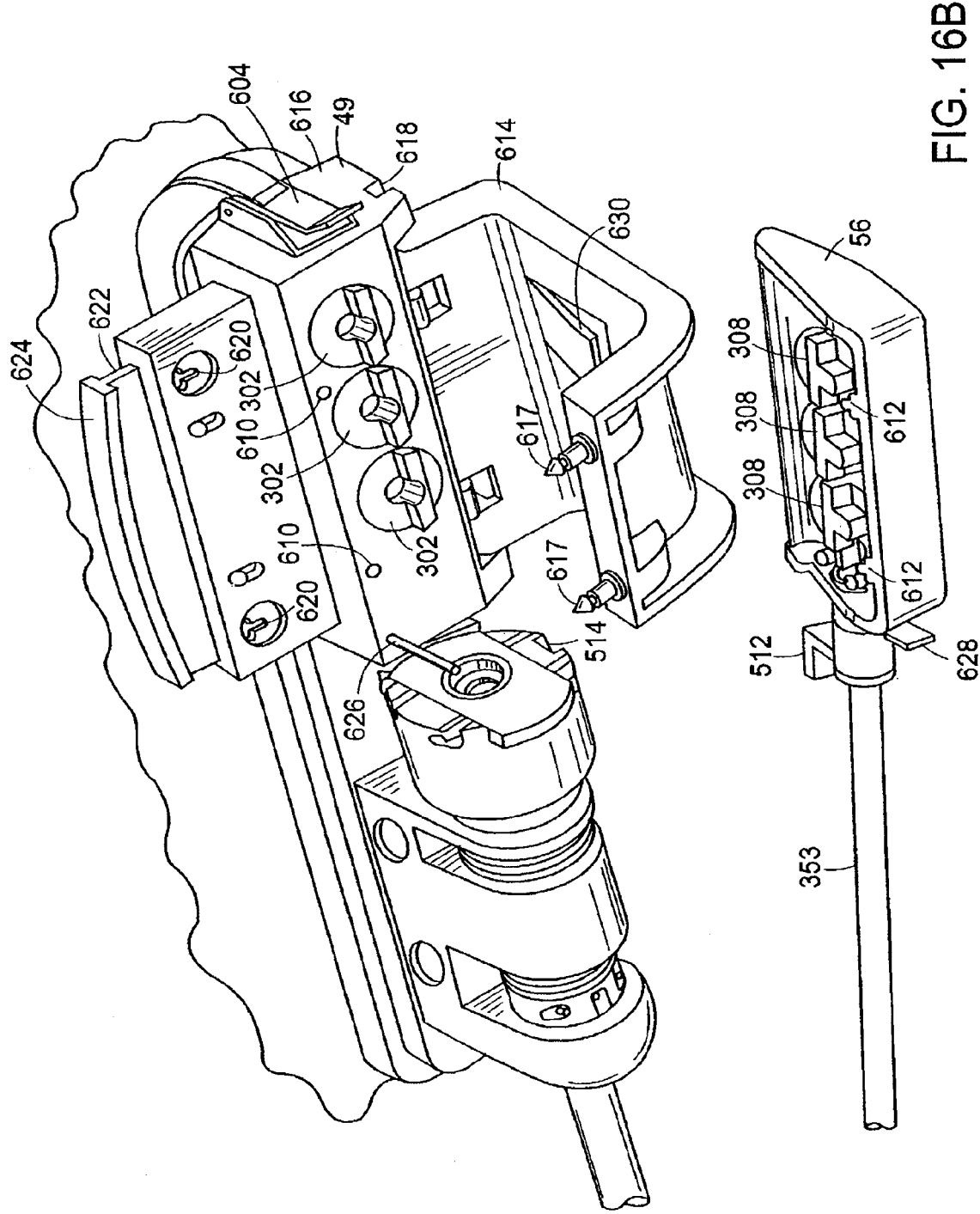
FIG. 16B is an exploded view of the instrument adapter and clamshell ready to receive a tool insert.

Referring to FIG. 16B, there is shown the insert 56 prior to insertion into the adaptor 49. The adaptor 49 includes alignment holes 610 for the corresponding nubs 612 of the insert 56. The adaptor 49 also includes a clamshell 614 attached to a base portion 616 with a pivot joint 618. The clamshell 614 is provided with a pair of pins 617 that engage with respective keyholes 620 of a catchplate 622. A clamshell release handle 624 is springloaded with a spring 625 (FIG. 10) to allow a user to release the clamshell 614 from the catchplate 622 by pushing on the handle 624.

Figure 17:
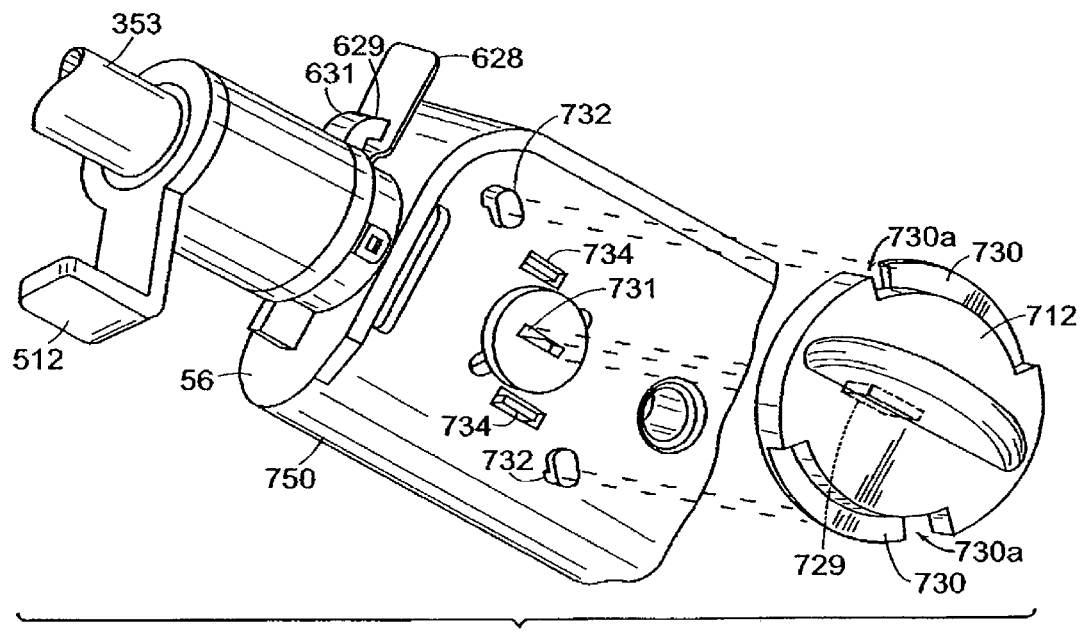
FIG. 17 is an exploded view of the underside of the instrument insert.

Referring also to FIG. 16C, after the shaft 353 is inserted into the guide tube 46, the drive arm 512 mates with the receiving slot 514 to couple the shaft 353 to the shaft drive pulley 354. In addition, a release pin 626 extending from the base portion 616 pushes against a flexure 628 to unlock the shaft 353 (FIG. 16B). Referring also to FIG. 17, the flexure 628 has a hole 629 in which a tab 631 is positioned before insertion. The tab 631 is attached to the shaft 353 such that as the flexure 628 is pushed away from the tab 631 the shaft 353 is free to rotate.

Figure 16E:
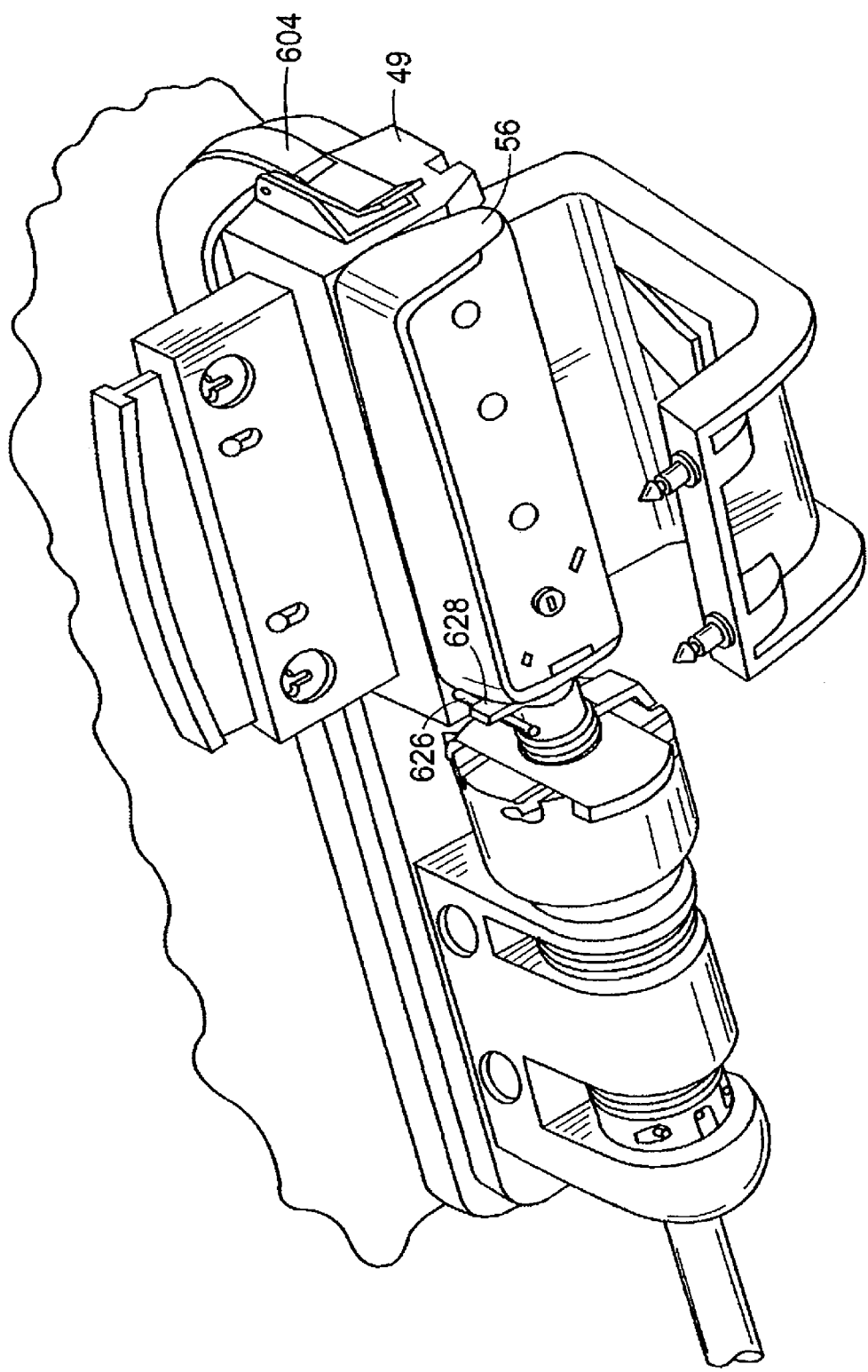
FIG. 16E is an exploded view of the instrument adapter and clamshell with the tool insert fully inserted into the guide shaft prior to closing the clamshell.

Referring also to FIG. 16D, as the insert 56 is rotated in place, the nubs 612 align and fit into the alignment holes 610 while the face 520 of the drive wheels 308 mate with the face 522 of the lower drive shafts 302. The clamshell 614 is provided with a spring 630 (FIGS. 10 and 16C) that pushes against the bottom of the insert 56 when the clamshell 614 is snapped into the locked position so that the insert 56 abuts against the adaptor 49 with an applied force. FIG. 16E illustrates the instrument insert 56 fully inserted, but with the clamshell 614 still open.

The adaptor 49, such as depicted in FIG. 16A, is readily attachable and detachable with the coupling mechanism such as the block and tackle assembly 64. This provides a more adaptable surgical system useable with a greater number of types of surgical procedures. For example, one of the primary differences from adaptor-to-adaptor may be the radius of curvature of the distal curved end of the guide tube 46. Also, the length of the curved section of the guide tube may be varied, or the combination of curvature and length can to taken into account in selecting different adaptors. Moreover, the diameter of the tube could be different depending upon size and diameter of the instrument insert. Furthermore, instead of providing a curvature at the distal end of the guide tube, there can be a straight bend at the distal end. Either a curvature, bend, or other deflection of the distal end of the guide tube provides the desired off-set of the distal end so that, upon rotary motion C-C of the guide tube, there is motion of the tool out of the plane defined by the pivoting base motion A-A.

For some surgical procedure, as mentioned above, it may be desirable to substitute different types of adaptors. For example, if a particular procedure requires work in both a focused small area, as well as in a broader extending area of the patient, it is desirable to use different types of adaptors. The different adaptors might have different lengths, diameters, curvatures, or combinations thereof.

Figure 18:
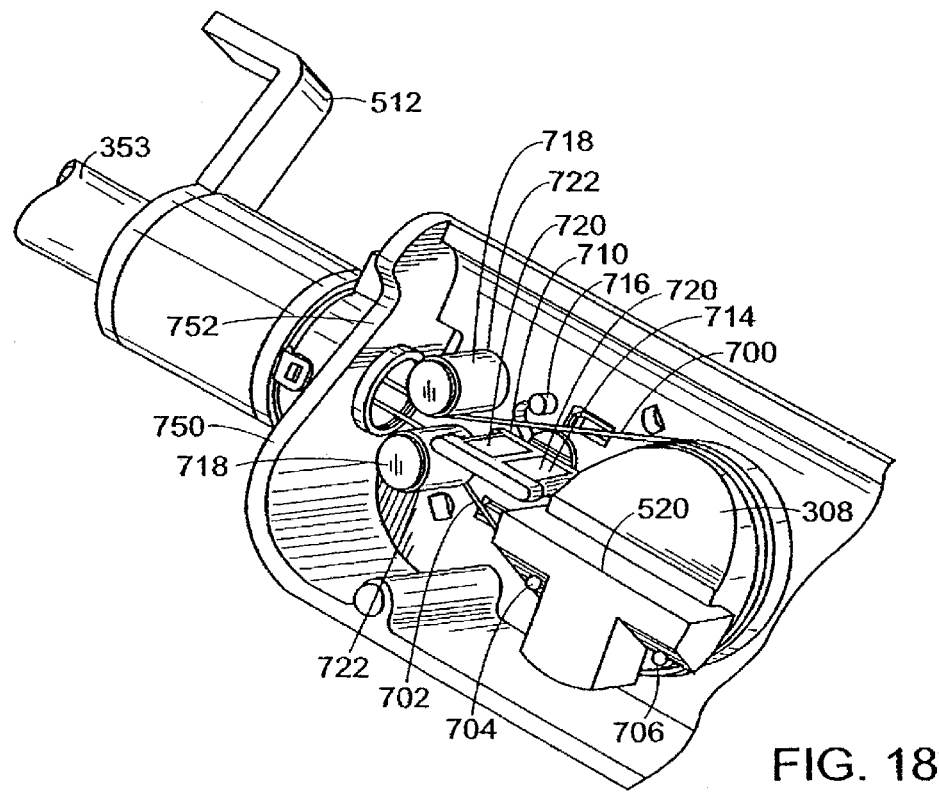
FIG. 18 is a detail view of a tensioning blade before engagement.

Details of the individual drive mechanisms of the insert 56 that provide the degrees of freedom of movement E-E, F-F, and G-G (FIG. 3) are illustrated in FIGS. 17 and 18, as well as FIG. 15. For each degree-of-freedom, a pair of cables 700 and 702 extends through the shaft 353 and is coupled at the terminal ends of the cables to the tool 44. The other ends of the cables 700 and 702 are attached to respective drive wheels 308 with cable anchors 704 and 706.

Illustrated in FIG. 18 is a tensioning mechanism 710 that is in a non-tensioned position when the insert 56 is not in use. The tensioning mechanism includes a tensioning handle 712 (FIG. 17) provided with a tab 729 on its underside that engages with a slot 731 on the bottom of a blade 714, and a pair of outer lips 730 that engage with a pair of undercuts 732 on the bottom of the insert housing 750.

Prior to inserting the insert 56 into the adaptor 49, a user turns the handle 712 about 90.degree. until the tension blade 714 rests against a stop pin 716, while a pair of spring-arm catches 734 snap up and latch the blade 714 in place. When this occurs, the blade 714 spreads the cables 700 and 702 apart such that they are pushed against a pair of cable guide posts 718 to pretension the cables 700 and 702. This pretension position of the blade 714 is shown in FIGS. 14 and 15. The handle 712 is provided with a pair of slots 730a that match up with the undercuts 732 so that when the handle has been turned approximately 90.degree. the handle can be removed from the insert 56. Note also that the housing 750 has a cutout 752 that provides a clearance while the insert 56 is being inserted into the adaptor 49.

The blade 714 can be made of plastic and is provided with smooth surfaces 720 made of, for example, stainless steel, so that the cables 700 and 702 are able to glide over the blade 714 with minimal friction. Similarly, the guide posts 718 are also provided with smooth surfaces 722 that minimize friction between the posts 718 and the cables 700 and 702.

While this invention has been particularly shown and described with references to preferred embodiments thereof, it will be understood by those skilled in the art that various changes in form and details may be made therein without departing from the scope of the invention encompassed by the appended claims. For example, although the slider mechanism is described in the context of a coupling mechanism, other embodiments in which the cable bundle is attached at its distal end at a stationary location are also considered within the scope of the present invention.

What is claimed is:

1. A medical system, comprising:
a surgical instrument configured for performing a medical procedure on a patient;
an adapter configured for removably receiving a proximal end of the surgical instrument; and
a drive unit configured for being coupled to the adapter to control the movement of the surgical instrument within at least one degree-of-freedom,
wherein the adapter has a driver element configured for being actuated by the drive unit, and the surgical instrument has a driven element configured for being actuated by the driver element to move the surgical instrument within the at least one degree-of-freedom, and
wherein the adapter has a base portion and a clam-shell that pivots relative to the base portion between a first position that encloses the proximal end of the surgical instrument within the adapter and a second position that allows the proximal end of the surgical instrument to be removed from the adapter.

2. The medical system of claim 1, further comprising a remote controller configured for directing the drive unit to control the movement of the surgical instrument within the at least one degree-of-freedom.

3. The medical system of claim 2, wherein the remote controller has a user interface for receiving commands from a user.

4. The medical system of claim 3, wherein movements made at the user interface correspond to movements of the surgical instrument.

5. The medical system of claim 2, wherein the remote controller is coupled to the drive unit via external cabling.

6. The medical system of claim 1, wherein the drive unit has a motor array.

7. The medical system of claim 1, further comprising a coupling mechanism through which the adapter is operably coupled to the drive unit.

8. The medical system of claim 7, wherein the coupling mechanism comprises a carriage on which the surgical instrument is slidably mounted.

9. The medical system of claim 1, wherein the driver element is a drive shaft, and the driven element is a wheel that mates with the drive shaft.

10. The medical system of claim 1, wherein the at least one degree-of-freedom is an actuation of a distal tool carried on a distal end of the surgical instrument.

11. The medical system of claim 1, wherein the at least one degree-of-freedom comprises a plurality of degrees-of-freedom.

12. The medical system of claim 1, wherein the adapter and the proximal end of the surgical instrument have corresponding mechanisms that align with each other when the proximal end of the surgical instrument is received within the adapter.

13. The medical system of claim 1, wherein the adapter has a catch mechanism configured for engaging the clam-shell in the first position.

14. The medical system of claim 13, wherein the adapter has a release mechanism configured for being actuated to disengage the clam-shell from the catch mechanism to place the clam-shell within the second position.

15. A surgical instrument adapter, comprising:
a base portion configured for receiving a proximal end of a surgical instrument;
a clam-shell that pivots relative to the base portion between a first position that encloses the proximal end of the surgical instrument within the base portion and a second position that allows the proximal end of the surgical instrument to be removed from the base portion; and
a driver element configured for actuating a driven element located at the proximal end of the surgical instrument to move the surgical instrument within at least one degree-of-freedom.

16. The surgical instrument adapter of claim 15, wherein the driver element is configured for being actuating by a drive unit located external to the adapter.

17. The surgical instrument adapter of claim 15, wherein the driver element is a drive shaft.

18. The medical instrument adapter of claim 15, wherein the at least one degree-of-freedom is an actuation of a distal tool carried by the medical instrument.

19. The medical instrument adapter of claim 15, wherein the at least one degree-of-freedom comprises a plurality of degrees-of-freedom.

20. The medical instrument adapter of claim 15, wherein the adapter has a mechanism configured for aligning the proximal end of the surgical instrument within the base portion.

21. The medical instrument adapter of claim 15, wherein the adapter has a catch mechanism configured for engaging the clam-shell in the first position.

22. The medical instrument adapter of claim 21, wherein the adapter has a release mechanism configured for being actuated to disengage the clam-shell from the catch mechanism to place the clam-shell in the second position.

* * * * *